(12) United States Patent
Park et al.

(10) Patent No.: US 9,585,376 B2
(45) Date of Patent: Mar. 7, 2017

(54) AUTOMATIC MONITORING OF INSECT POPULATIONS

(75) Inventors: Johnny Park, Lafayette, IN (US); German Andres Holguin Londono, West Lafayette, IN (US); Henry Ponti Medeiros, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 872 days.

(21) Appl. No.: 13/879,685

(22) PCT Filed: Oct. 17, 2011

(86) PCT No.: PCT/US2011/056555
§ 371 (c)(1),
(2), (4) Date: Apr. 16, 2013

(87) PCT Pub. No.: WO2012/054397
PCT Pub. Date: Apr. 26, 2012

(65) Prior Publication Data
US 2013/0204581 A1 Aug. 8, 2013

Related U.S. Application Data

(60) Provisional application No. 61/393,919, filed on Oct. 17, 2010.

(51) Int. Cl.
*A01M 1/22* (2006.01)
*A01N 61/00* (2006.01)
(Continued)

(52) U.S. Cl.
CPC ............ *A01M 1/223* (2013.01); *A01M 1/026* (2013.01); *A01M 1/2016* (2013.01); *A01N 61/00* (2013.01)

(58) Field of Classification Search
CPC .... A01M 1/223; A01M 1/026; A01M 1/2016; A01M 1/2011; A01M 31/002; A01M 1/14; A01M 1/023; A01N 61/00
See application file for complete search history.

(56) References Cited

U.S. PATENT DOCUMENTS

| 4,179,839 A | 12/1979 | Salotti et al. |
| 4,275,523 A | 6/1981 | Baima et al. |

(Continued)

FOREIGN PATENT DOCUMENTS

| CN | 101554150 A | 10/2009 |
| CN | 101840214 A | 9/2010 |

(Continued)

OTHER PUBLICATIONS

Rajagopalan et al. Data aggregation techniques in sensor networks: A survey, Jan. 1, 2006, Syracuse University, pp. 1-31.*

(Continued)

*Primary Examiner* — John Breene
*Assistant Examiner* — Mohammad Islam
(74) *Attorney, Agent, or Firm* — Barnes & Thornburg LLP

(57) ABSTRACT

Illustrative embodiments of integrated pest management (IPM) systems and electronic insect monitoring devices (EIMDs) are disclosed. In some embodiments, the EIMDs may each comprise a lure for attracting at least one target insect species, one or more sensors that generate one or more output signals in response to an insect approaching the lure, and an electronic controller configured to determine if the insect approaching the lure belongs to the at least one target insect species using the one or more output signals. In some embodiments, the IPM system may comprise a plurality of EIMDs configured to communicate over a wireless network shared by the plurality of EIMDs.

21 Claims, 16 Drawing Sheets

(51) Int. Cl.
   *A01M 1/02* (2006.01)
   *A01M 1/20* (2006.01)

(56) References Cited

U.S. PATENT DOCUMENTS

| | | | |
|---|---|---|---|
| 4,410,967 A | 10/1983 | Hendricks | |
| 5,343,652 A | 9/1994 | Johnson | |
| 5,417,009 A * | 5/1995 | Butler | A01M 1/08 43/113 |
| 6,124,826 A * | 9/2000 | Garthwaite | G01C 21/3423 340/995.12 |
| 6,134,826 A * | 10/2000 | Mah | A01M 1/04 43/112 |
| 6,216,383 B1 * | 4/2001 | Klabunde | A01M 1/02 43/107 |
| 6,564,503 B1 | 5/2003 | Miyahara et al. | |
| 6,978,572 B1 * | 12/2005 | Bernklau | A01M 1/023 43/107 |
| 7,212,112 B2 | 5/2007 | Barber et al. | |
| 8,479,438 B1 * | 7/2013 | Wilhelmi | A01M 1/106 43/121 |
| 8,978,290 B2 * | 3/2015 | Wright | A01M 1/02 43/113 |
| 2002/0185605 A1 * | 12/2002 | Shuman | G01N 15/1456 250/341.7 |
| 2004/0093190 A1 * | 5/2004 | Beroza | A01M 1/026 702/189 |
| 2005/0025357 A1 | 2/2005 | Landwehr et al. | |
| 2005/0063956 A1 * | 3/2005 | Bernklau | A01M 1/023 424/93.4 |
| 2006/0150470 A1 * | 7/2006 | Ronnau | A01M 1/026 43/58 |
| 2007/0169401 A1 * | 7/2007 | Chyun | A01M 1/145 43/113 |
| 2008/0148624 A1 * | 6/2008 | Borth | G01N 33/68 43/131 |
| 2008/0181352 A1 * | 7/2008 | Hirafuji | A01M 1/026 377/16 |
| 2009/0199457 A1 | 8/2009 | Grigorov et al. | |
| 2009/0220428 A1 * | 9/2009 | Grau | A01N 47/44 424/9.2 |
| 2010/0071254 A1 | 3/2010 | Calkins et al. | |
| 2011/0030266 A1 * | 2/2011 | Roy | A01M 1/08 43/113 |
| 2011/0138678 A1 * | 6/2011 | Smith | A01M 1/023 43/107 |
| 2011/0290909 A1 * | 12/2011 | White | A01N 35/02 239/44 |
| 2012/0269900 A1 * | 10/2012 | Watkinson | A01N 25/00 424/646 |

FOREIGN PATENT DOCUMENTS

| | | |
|---|---|---|
| EP | 1 652 428 A1 | 9/2000 |
| JP | 11-155458 A | 6/1999 |
| JP | 2003-304788 A | 10/2003 |
| JP | 2005-21074 A | 1/2005 |
| KR | 1020100097096 A | 9/2010 |
| WO | 2008/133830 A2 | 11/2008 |

OTHER PUBLICATIONS

Dyo, Adaptive Duty Cycling in Mobile Sensor Networks, 2009, pp. 1-24.*
PCT Search Report and Written Opinion for PCT/US2011/056555, completed Feb. 29, 2012.
IP Australia, First Office Action for Australian Patent Application No. 2011317278, May 19, 2014, 5 pages.
State Intellectual Property Office, P.R. China, Second Office Action for Patent Application No. 201180063662.8, Sep. 28, 2014, 15 pages (including translation).
Columbian Industrial Property Office, First Office Action for CO 13-98053, Mar. 7, 2014, 17 pages.
Chesmore et al., "Acoustic Methods for the Automated Detection and Identification of Insects", Proc. Sensors in Hort. III, 2001, pp. 223-231.
Automata, Inc., "Bug Counter Remote Counting of Insects," Oct. 15, 2003, 2 pages.
Mayo et al., "Automatic Species Identification of Live Moths", Knowledge-Based Sys., 2007, 14 pages.
Shi, "Still Image Coding Standard: JPEG," Image and Video Compression for Multimedia Engineering: Fundamentals, Algorithms, and Standards, 2000, 12 pages.
"NMSU: Integrating Biological Control—Projects," available at http://aces.nmsu.edu/academics/ibc/projects.html, 6 pages.
Richenbach et al., "Gathering Correlated Data in Sensor Networks", Oct. 1, 2004, pp. 60-66.
Pattem et al., "The Impact of Spatial Correlation on Routing with Compression in Wireless Sensor Networks", Apr. 2004, pp. 28-35.
Intanagonwiwat et al., "Impact of Network Density Aggregation in Wireless Sensor Networks", USC/Information Sciences Institute, Nov. 4, 2001, pp. 1-16.
Marvell Semiconductor, Inc., "Marvell Plug Computer Development Kit," 2010, 2 pages.
Mhatre et al., "A Minimum Cost Heterogeneous Sensor Network with a Lifetime Constraint", IEEE Transactions on Mobile Computing, vol. 4, No. 1, Jan./Feb. 2005, pp. 4-15.
Heinzelman et al., "Energy-Efficient Communication Protocol for Wireless Microsensor Networks", 2000 IEEE, Proceedings of the Hawaii International Conference on System Sciences, Jan. 2000, pp. 1-10.
Kalpakis et al., "Efficient Algorithms for Maximum Lifetime Data Gathering and Aggregation in Wireless Sensor Networks", Computer Networks, vol. 42, 2003, pp. 697-716.
Moore et al., "Automated Identification of Flying Insects by Analysis of Wingbeat Frequencies", J. Econ. Entomol., 1986, pp. 1703-1706, vol. 79.
Heinzelman et al., "An Application-Specific Protocol Architecture for Wireless Microsensor Networks", IEEE Transactions on Wireless Communications, Oct. 2002, pp. 660-670, vol. 1, No. 4.
Ganchev et al., "Acoustic Monitoring of Singing Insects," Proceedings of IEEE ICASSP-2007, pp. 721-724, vol. 4.
Xia et al., "Near-Optimal Node Clustering in Wireless Sensor Networks for Environmental Monitoring", 21st International Conference on Advanced Networking and Applications, 2007, 10 pages.
Langendoen et al., "Distributed Localization in Wireless Sensor Networks: A Quantitative Comparison", Computer Networks, 2003, pp. 499-518, vol. 43.
Hendricks, "Electronic Systems to Automatically Detect Insect Pests that Respond to Species-Specific Chemical Sex Pheromone Baits", IEEE International Workshop on Intelligent Robots and Systems, 1990, pp. 287-293.
Marcelloni et al., "An Efficient Lossless Compression Algorithm for Tiny Nodes of Monitoring Wireless Sensor Networks", The Computer Journal, Apr. 30, 2009, pp. 1-19.
Moore et al., "Automated Identification of Optically Sensed Aphid (*Homoptera aphidae*) Wingbeat Waveforms", Annals of the Entomological Society of America, 2002, pp. 1-8, vol. 95.
Medeiros et al., "A Light-Weight Even-Driven Protocol for Sensor Clustering in Wireless Camera Networks", First ACM/IEEE International Conference on Distributed Smart Cameras, Sep. 2007, 8 pages.
Medeiros et al., "Distributed Object Tracking Using a Cluster-Based Kalman Filter in Wireless Camera Networks", IEEE Journal of Selected Topics in Signal Processing, Aug. 2008, pp. 448-463, vol. 2, No. 4.
Shuman et al., "A Computer-Based Electronic Fall-Through Probe Insect Counter for Monitoring Infestation in Stored Products", Transactions of the American Society of Agricultural Engineers, 1996, pp. 1773-1780, vol. 39(5).
Savvides et al., "Dynamic Fine-Grained Localization in Ad-Hoc Wireless Sensor Networks", Center for Embedded Network Sensing, University of California, May 5, 2001, pp. 166-179.

(56) References Cited

OTHER PUBLICATIONS

Watson et al., "Automated Identification of Live Moths (*Macrolepidoptera*) using Digital Automated Identification System (DAISY)", Systematics and Biodiversity, 2003, pp. 287-300, vol. 1:3.

IEEE, "Standard for Local and Metropolitan Area Networks—Part 15.4: Low-Rate Wireless Personal Area Networks (LR-WPANs)," 2011, 334 pages.

He et al., "Range-Free Localization Schemes for Large Scale Sensor Networks", Proc. 9th Ann. Int'l Conf. on Mobile Computing & Networking, Sep. 2003, pp. 81-95.

Savarese et al., "Locationing in Distributed Ad-Hoc Wireless Sensor Networks", 4 Proc. IEEE Int'l Conf. on Acoustics, Speech, & Signal Processing, 2001, pp. 2037-2040.

Mhatre et al., "Design of Surveillance Sensor Grids with a Lifetime Constraint", Eur. Workshop on Wireless Sensor Networks, 2004, 13 pages.

Gupta et al., "Cluster-Head Election Using Fuzzy Logic for Wireless Sensor Networks", Comm'n. Networks & Servs. Res. Conf., 2005, pp. 255-260.

Younis et al., "HEED: A Hybrid, Energy-Efficient, Distributed Clustering Approach for Ad-Hoc Sensor Networks", IEEE Transactions on Mobile Computing, 2004, 36 pages.

Krishnamachari et al., "Impact of Data Aggregation in Wireless Sensor Networks", Distributed Computing Sys. Workshops, 2002, 9 pages.

Graetzel et al., "A 6000 Hz Computer Vision System for Real-Time Wing Beat Analysis of *Drosophila*", Robotics & Biomechatronics, 2006, pp. 278-283.

Medeiros et al., "Cluster-Based Object Tracking by Wireless Camera Networks", Multi-Camera Networks: Concepts & Applications, 2009, pp. 539-572.

State Intellectual Property Office, P.R. China, First Office Action for Patent Application No. 201180063662.8, Jan. 21, 2014, 26 pages (including translation).

New Zealand Intellectual Property Office, First Examination Report for Application No. 608703, Nov. 7, 2013, 2 pages.

Extended European Search Report, European Application No. 11834936.4-1656 / 2627170 PCT/US2011056555, dated Oct. 31, 2016, 8 pages.

\* cited by examiner

AUTOMATIC MONITORING OF INSECT POPULATIONS

CROSS REFERENCE TO RELATED APPLICATION

This application is a national stage entry under 35 U.S.C. §371(b) of International Application No. PCT/US2011/056555, filed Oct. 17, 2011, which claims priority to U.S. Provisional Application No. 61/393,919, filed Oct. 17, 2010, the entire disclosures of which are hereby incorporated by reference.

GOVERNMENT RIGHTS

Part of the work during the development of this invention was funded with government support from the National Institute of Food and Agriculture under grant SCRI-103480; the United States Government may have certain rights in the invention.

TECHNICAL FIELD

The present disclosure relates, generally, to integrated pest management (IPM) systems and, more particularly, to wireless sensor networks for the automatic monitoring of insect populations.

BACKGROUND ART

A consensus exists among government agencies, research institutions, industry, grower organizations, and the general public that regularly scheduled applications of broad-spectrum pesticides should be reduced, as these pesticides give rise to a number of economical, environmental, and social issues (e.g., overuse of pesticides, pesticide resistance, toxicity to natural enemies, worker safety, food residues, etcetera). Developing IPM programs based on ecologically sound technologies offers a unique opportunity toward meeting this and other needs.

Monitoring insect populations is an important component in any ecologically sound IPM program. For example, if a grower underestimates an insect population to be below a treatment threshold, the grower may not apply pesticide even though there are enough insects to cause serious fruit damage. On the other hand, if the grower overestimates the insect population to be above the treatment threshold when it is actually below the treatment threshold, the grower may waste money and resources by applying unnecessary pesticides.

In the tree fruit industry, the most economically significant insects are moths, including, but not limited to, codling moths (*Cydia pomonella*), Oriental fruit moths (*Grapholita molesta*), and leafrollers (*Archips argyrospila* and *Choristoneura rosaceana*). In the stored product industry, moths and beetles are the two major pests, including, but not limited to, Indianmeal moths (*Plodia interpunctella*), Mediterranean flour moths (*Ephestia kuehniella*), cigarette beetles (*Lasioderma serricorne*), and warehouse beetles (*Trogoderma variabile*). For each of these insects, artificial lures have been developed based on the specific sex pheromone that the female of each species uses to attract males for mating. During the last three to four decades, the capture of male moths in pheromone-baited traps has been the most principled measure utilized to control insect populations and to inform pest management decisions (e.g., when to initiate a pesticide treatment, where and how much pesticide to apply, etcetera). Such techniques have permitted a relatively large decrease in the number of pesticide applications, as described in M. G. Solomon, Integrated Pest Management (1987); O. B. Kovanci et al., Comparison of Mating Disruption with Pesticides for Management of Oriental Fruit Moth (Lepidoptera: Tortricidae) in North Carolina Apple Orchards, J. Econ. Entomology 1248-58 (2005); D. Thomson et al., Ten Years Implementing Codling Moth Mating Disruption in the Orchards of Washington and British Columbia: Starting Right and Managing for Success, IOBC WPRS Bulletin 23-30. (2001); T. Alway, Codling Moth Mating Disruption and Establishing a Pheromone-Based Codling Moth Management Site in the Pacific Northwest, Wash. State Univ. (1998); L. J. Gut et al., Pheromone-Based Management of Codling Moth (Lepidoptera: Tortricidae) in Washington Apple Orchards, J. Agric. Entomology 387-405 (1998); and L. H. Blommers, Integrated Pest Management in European Apple Orchards, 39 Ann. Rev. Entomology 213-41 (1994), the entire disclosures of which are each incorporated by reference herein.

Despite the potential benefit, the labor-intensive activities associated with managing pheromone traps have been a key factor slowing down their widespread adoption. It is typically recommended that pheromone traps be distributed at densities of one trap per hectare (i.e., about 100 m apart) for tree fruit pests and one trap per 100 m$^2$ (i.e., about 10 m apart) for stored product pests. Additional traps are often needed around the border and other areas susceptible to new pest immigrations. Currently, pheromone traps need to be inspected on a regular basis—typically one to five times per week depending on the time of the season and the pest species. Trap inspection typically consists of (1) locating individual traps, (2) manually counting the number of target pests captured in each trap and writing the number down on a piece of paper, and (3) replacing the sticky bottom in each trap, as insects and other debris cover the sticky bottom. As such, the labor costs associated with pheromone traps can easily become prohibitively expensive (i.e., greater than any savings realized from pesticide reduction). These labor costs have been documented in S. C. Welter, Range of Attraction for Modified Pheromone Ttrap-Lure Combinations for Mating Disruption Orchards, Calif. Pear Advisory Bd. (1997); E. R. Williamson et al., Economics of Employing Pheromones for Mating Disruption of the Codling Moth, *Carpocapsa Pomonella*, Crop Protection 473-477 (1996); L. H. Blommers (cited above); and P. G. Fenemore et al., Problems of Implementing Improvements in Pest Control: A Case Study of Apples in the UK, Crop Protection 51-70 (1985), the entire disclosures of which are each incorporated by reference herein. Constant monitoring of insect populations thus remains one of the most challenging components of any IPM program.

DISCLOSURE OF INVENTION

According to one aspect, an electronic insect monitoring device (EIMD) may comprise a lure for attracting at least one target insect species, one or more sensors that generate one or more output signals in response to an insect approaching the lure, and an electronic controller configured to determine if the insect approaching the lure belongs to the at least one target insect species using the one or more output signals.

In some embodiments of the EIMD, the one or more sensors may comprise a bio-impedance sensor. The bio-impedance sensor may comprise a high-voltage electric discharge grid. The high-voltage electric discharge grid may comprise a plurality of metallic elements that define a cylinder with an open bottom surface. The high-voltage electric discharge grid may be configured to produce a voltage that only temporarily stuns an insect that approaches the lure. In other embodiments of the EIMD, the one or more sensors may comprise an optical sensor. In still other embodiments of the EIMD, the one or more sensors may comprise an ultrasonic sensor. In some embodiments, the one or more sensors may comprise at least two sensors selected from the group consisting of ultrasonic sensors, bio-impedance sensors, and optical sensors.

In some embodiments of the EIMD, the electronic controller may be configured to determine if the insect approaching the lure belongs to the at least one target insect species by analyzing at least one of a slope, an amplitude, a rise time, a fall time, a width, and a ringing frequency of an electrical pulse of the one or more output signals. In other embodiments of the EIMD, the electronic controller may be configured to determine if the insect approaching the lure belongs to the at least one target insect species by applying a sensor fusion algorithm to the one or more output signals.

In some embodiments, the EIMD may further comprise a communication module for wirelessly communicating with neighboring EIMDs. In other embodiments, the EIMD may further comprise a global positioning system module for determining a deployment location of the EIMD. In still other embodiments, the EIMD may further comprise a battery that supplies power to the electronic controller and to the one or more sensors via a power controller. The power controller may be configured to implement an active duty-cycling scheme to conserve the power supplied by the battery.

In some embodiments, the EIMD may further comprise an insect collector having at least one inwardly sloped upper surface. In other embodiments, the EIMD may further comprise a housing containing the electronic controller. The housing may be configured to be interchangeably fitted with one of a delta-shaped insect collector and a bucket-shaped insect collector.

According to another aspect, an integrated pest management (IPM) system may comprise a plurality of electronic insect monitoring devices (EIMDs). Each of the plurality of EIMDs may comprise one or more sensors configured to detect a target insect, an electronic controller configured to count a number of target insects detected during a time period, and a wireless radio configured to communicate the number of target insects detected during the time period over a wireless network shared by the plurality of EIMDs.

In some embodiments of the IPM system, each of the plurality of EIMDs may further comprise a global positioning system module configured to determine a location of the EIMD. The wireless radio of each of the plurality of EIMDs may be further configured to communicate the location of the EIMD over the wireless network. The wireless radio of each of the plurality of EIMDs may be configured to directly communicate over the wireless network with only a first subset of the plurality of EIMDs. The wireless radio of each of the plurality of EIMDs may be configured to indirectly communicate over the wireless network with a second subset of the plurality of EIMDs using multiple-hop communications.

In some embodiments of the IPM system, the electronic controller of each of the plurality of EIMDs may be configured to apply a cluster-based data aggregation protocol to data communicated over the wireless network. In other embodiments of the IPM system, the electronic controller of each of the plurality of EIMDs may be configured to apply an opportunistic data aggregation protocol to data communicated over the wireless network. In still other embodiments of the IPM system, the electronic controller of each of the plurality of EIMDs may be configured to apply a multidimensional data compression protocol to data communicated over the wireless network.

In some embodiments, the IPM system may further comprise a decision support system (DSS) configured to receive the number of target insects detected by each of the plurality of EIMDs and to output site-specific pest management information in response to the number of target insects detected by each of the plurality of EIMDs. The IPM system may further comprise a network gateway in direct communication with the DSS, the network gateway configured to communicate with one or more of the plurality of EIMDs over the wireless network. In other embodiments, the IPM system may further comprise an embedded base station configured to communicate with one or more of the plurality of EIMDs over the wireless network and to communicate with the DSS over a public network.

In some embodiments of the IPM system, the site-specific pest management information may comprise a graphical user interface that includes an insect population map. The graphical user interface may further include one or more icons that each represent the location of one of the plurality of EIMDs. The graphical user interface may also include a graph illustrating the number of target insects detected by one or more of the plurality of EIMDs during the time period.

BRIEF DESCRIPTION OF DRAWINGS

The detailed description below particularly refers to the accompanying figures in which.

Similar elements are labeled using similar reference numerals throughout the figures.

BEST MODE(S) FOR CARRYING OUT THE INVENTION

Figure 1:
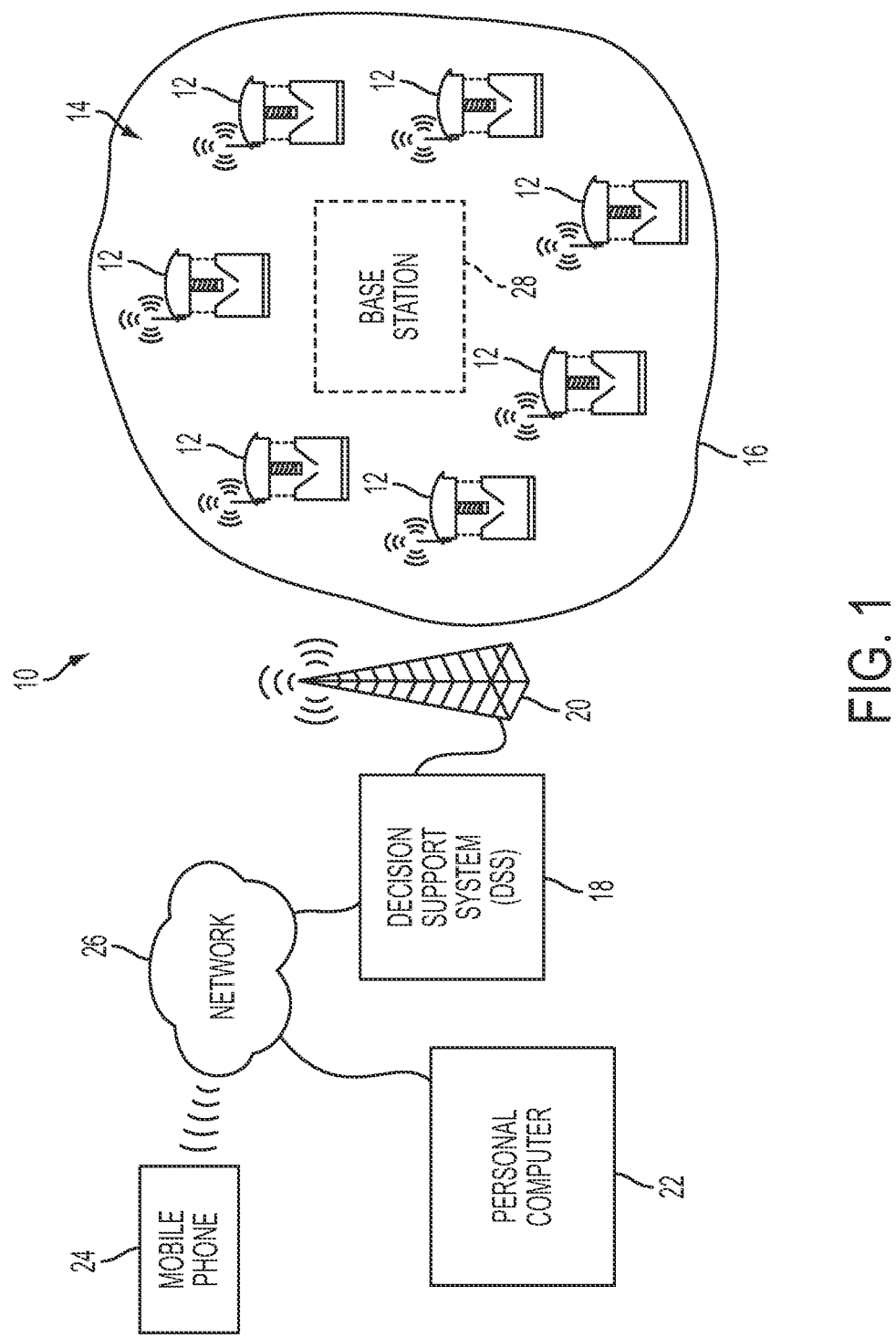
FIG. 1 illustrates one embodiment of an automated IPM system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

In the following description, numerous specific details, such as the types and interrelationships of system components, may be set forth in order to provide a more thorough understanding of the present disclosure. It will be appreciated, however, by one skilled in the art that embodiments of the disclosure may be practiced without such specific details. In other instances, control structures, gate level circuits, and full software instruction sequences may not have been shown in detail in order not to obscure the disclosure. Those of ordinary skill in the art, with the included descriptions, will be able to implement appropriate functionality without undue experimentation.

References in the specification to "one embodiment," "an embodiment," "an illustrative embodiment," etcetera, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Embodiments of the disclosure may be implemented in hardware, firmware, software, or any combination thereof. For instance, some illustrative embodiments of the disclosure may be implemented as instructions stored on one or more non-transitory, machine-readable media, which may be read and executed by one or more processors. A non-transitory, machine-readable medium may include any tangible mechanism for storing or transmitting information in a form readable by a machine (e.g., a processor). For example, a non-transitory, machine-readable medium may include read only memory (ROM), random access memory (RAM), magnetic disk storage media, optical storage media, flash memory devices, and other tangible media.

One illustrative embodiment of an automated integrated pest management (IPM) system 10 is shown in FIG. 1. The IPM system 10 includes a number of electronic insect monitoring devices (EIMDs) 12, forming an EIMD network 14 deployed in a field 16 (e.g., an orchard). It is contemplated that the EIMD network 14 may be deployed in any location where the IPM system 10 will provide improved pest management. Each EIMD 12 automatically monitors the insect population in its neighborhood using a lure (e.g., a sex pheromone) that attracts at least one target insect species and one or more electronic sensors that detect when a target insect enters approaches the lure. Various embodiments of EIMDs 12 that may be used in the IPM system 10 are described below with reference to FIGS. 2-10. It is contemplated that the IPM system 10 may include any number of EIMDs 12, depending on the characteristics of the deployment location (e.g., the size of the field 16).

In the illustrative embodiment of FIG. 1, the data acquired by each EIMD 12 is wirelessly transmitted to a decision support system (DSS) 18 via a network gateway 20 of the IPM system 10. The DSS 18 may be embodied as any type of computing device, or any number of computing devices. For example, the DSS 18 may be embodied as one or more personal computers, workstations, laptop computers, handheld computers, mobile internet devices, cellular phones, personal data assistants, telephony devices, network appliances, virtualization devices, storage controllers, or other computer-based devices configured to communicate with the EIMD network 14. In the illustrative embodiment of FIG. 1, the network gateway 20 is within the communications range of at least one EIMD 12 deployed in the field 16 (allowing the remaining EIMDs 12 to communicate indirectly with the network gateway 20 via multiple-hop routes, as will be further described below with reference to FIGS. 12, 13A, and 13B). In other embodiments, where the DSS 18 and network gateway 20 cannot be conveniently located in or near the field 16, the IPM system 10 may also include an embedded base station 28 deployed in the field 16. As will be further described below with reference to FIG. 11, the base station 28 is capable of collecting data from the EIMD network 14 without direct connection to an external computer or power supply.

The DSS 18 interprets data received from the EIMD network 14 and generates site-specific pest management information related to the field 16. For instance, the DSS 18 may generate one or more graphical user interfaces (GUIs), such as those described below with reference to FIGS. 14A, 14B, and 15, using the data received from the EIMD network 14. Users may access the site-specific pest management information generated by the DSS 18 via one or more browser-enabled computing devices, such as a personal computer 22 or a mobile phone 24. The one or more computing devices 22, 24 may be embodied as one or more personal computers, workstations, laptop computers, handheld computers, mobile internet devices, cellular phones, personal data assistants, telephony devices, network appliances, virtualization devices, storage controllers, or other computer-based devices configured to communicate with the DSS 18 over a network 26. The network 26 may be embodied as any type of wired and/or wireless network such as a local area network, a wide area network, a publicly available global network (e.g., the Internet), and/or other network. Additionally, the network 26 may include any number of additional devices to facilitate communication between the DSS 18 and the one or more computing devices 22, 24, such as routers, switches, intervening computers, and the like.

Figure 2:
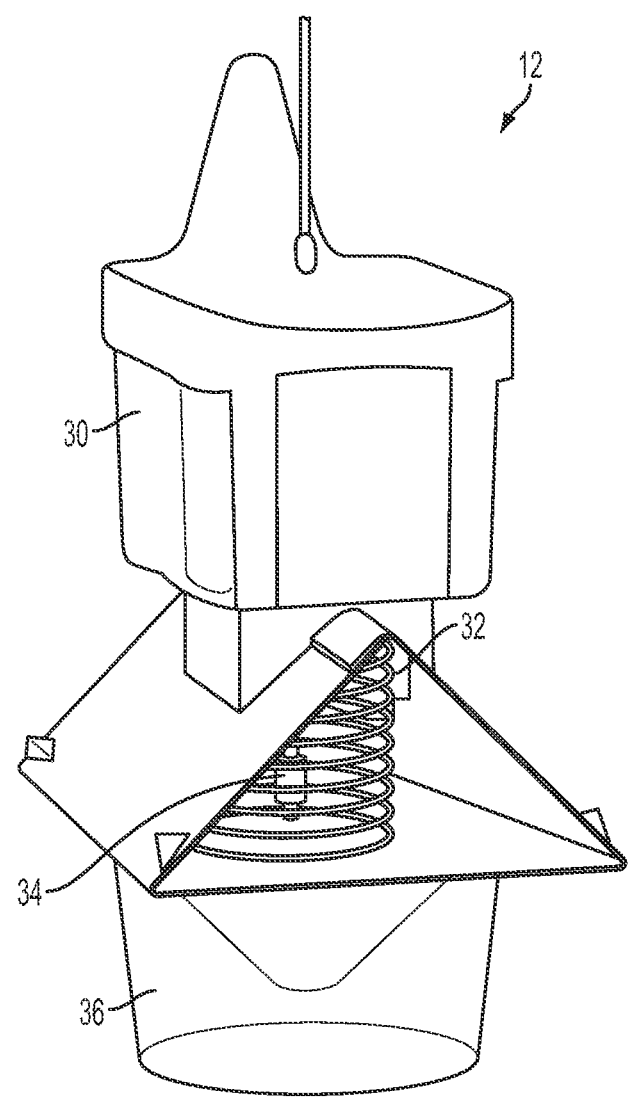
FIG. 2 illustrates one embodiment of an electronic insect monitoring device (EIMD) that may be used in the IPM system of FIG. 1.
Figure 3A:
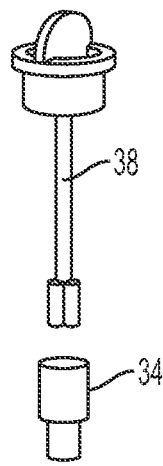
FIG. 3A illustrates one embodiment of a lure that may be used in the EIMD of FIG. 2.
Figure 3B:
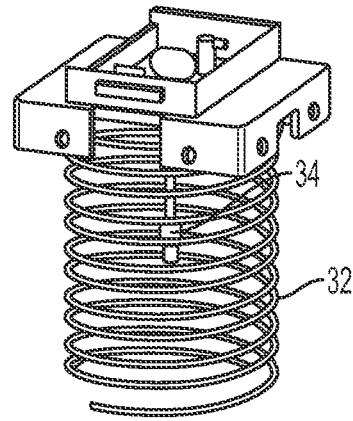
FIG. 3B illustrates one embodiment of a bio-impedance sensor that may be used in the EIMD of FIG. 2.

In the illustrative embodiments, each EIMD 12 of the IPM system 10 includes several modular components: an electronics housing 30, one or more sensors 32, one or more lures 34, and an insect collector 36. One illustrative embodiment of an EIMD 12 having these four modular components is shown in FIG. 2. The electronics housing 30 of the EIMD 12 encloses a mixed circuit board 40 (i.e., an analog and digital circuit) that, together with the one or more sensors 32, detects and identifies target insects and reports gathered data to the network gateway 20 (or to the base station 28). The one or more sensors 32 of the EIMD 12 may be embodied as any type of electronic sensors that generate one or more output signals in response to the presence of an insect. The one or more lures 34 of the EIMD 12 may be embodied as any type of substance (e.g., a sex pheromone) designed to attract a target insect. In some embodiments, the EIMD 12 may include multiple, non-interfering lures 34 for different target insect species (e.g., one lure 34 for codling moth and another lure 34 for Oriental fruit moth). As shown in FIG. 3A, the one or more lures 34 may be attached to a support 38 that allows the one or more lures 34 to be suspended amongst the one or more sensors 32 of the EIMD 12. The insect collector 36 of the EIMD 12 is generally positioned below the one or more sensors 32 and collects targets insects that are attracted by the one or more lures 34.

Figure 3C:
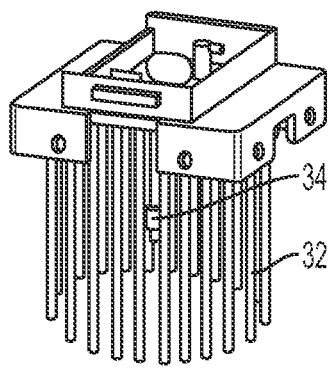
FIG. 3C illustrates another embodiment of a bio-impedance sensor that may be used in the EIMD of FIG. 2.
Figure 3D:
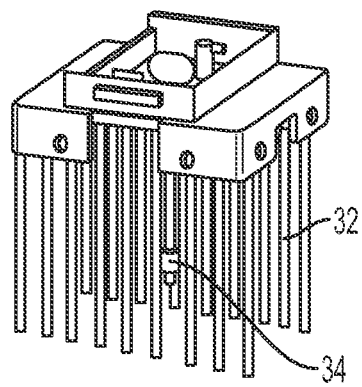
FIG. 3D illustrates yet another embodiment of a bio-impedance sensor that may be used in the EIMD of FIG. 2.
Figure 3E:
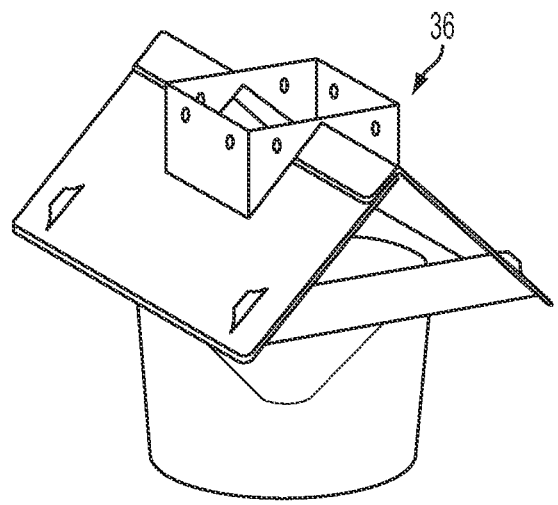
FIG. 3E illustrates one embodiment of an insect collector that may be used in the EIMD of FIG. 2.
Figure 3F:
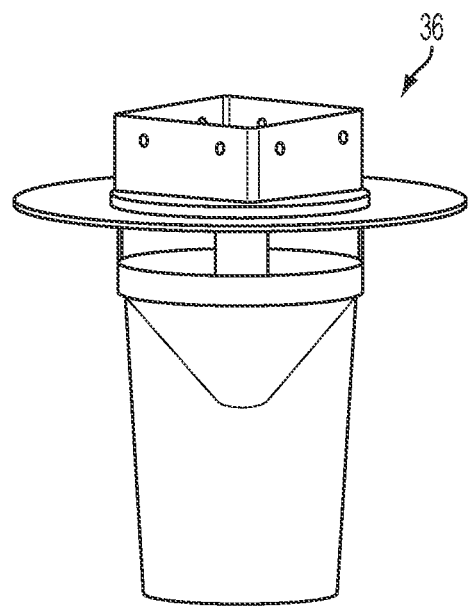
FIG. 3F illustrates another embodiment of an insect collector that may be used in the EIMD of FIG. 2.
Figure 4:
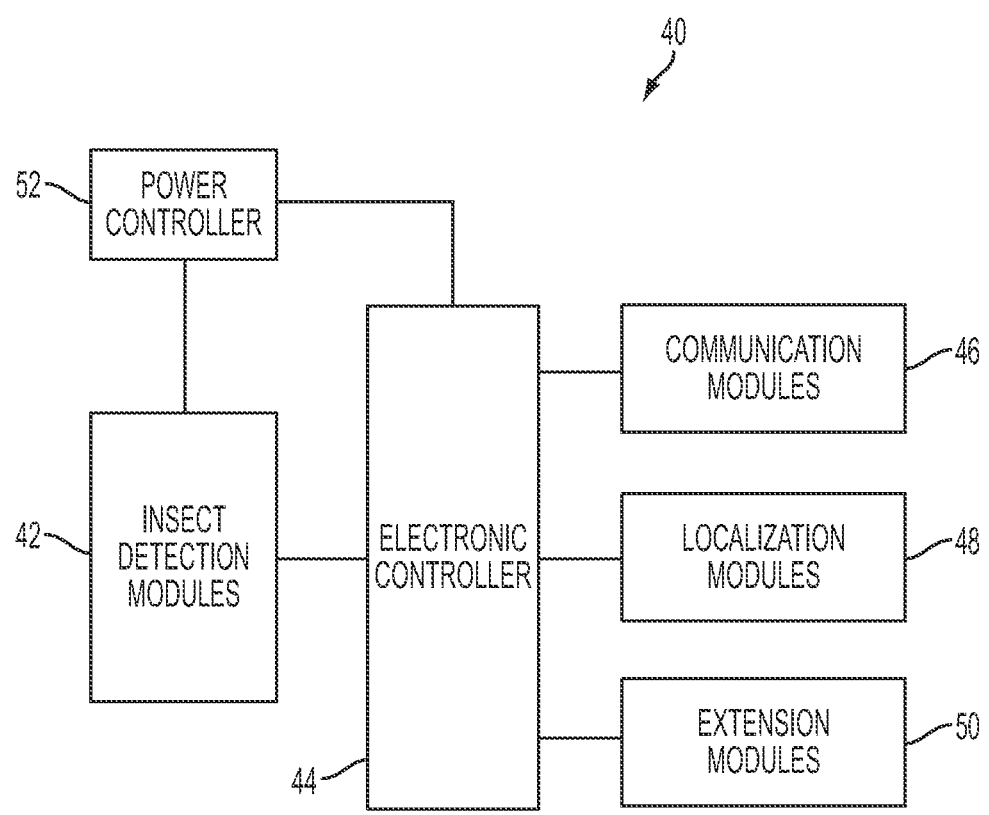
FIG. 4 is a simplified block diagram of one illustrative embodiment of a mixed circuit board that may be used in the EIMD of FIG. 2.

As the components of the EIMD 12 are modular, many different types of sensors 32, lures 34, and insect collectors 36 may be combined with the electronics housing 30 to assemble an EIMD 12 that targets a particular type of insect or achieves a desired performance. For instance, the one or more sensors 32 of the EIMD 12 may be embodied as one or more bio-impedance sensors, optical sensors, ultrasound sensors, and the like. In the illustrative embodiment shown in FIG. 2, the one or more sensors 32 comprise a bio-impedance sensor that is embodied as a high-voltage electric discharge grid 32. This particular bio-impedance sensor 32, which is shown in more detail in FIG. 3B, comprises two concentric metallic coils forming a cylinder with an open bottom surface. Alternative designs of the high-voltage electric discharge grid 32 are also contemplated. As shown in FIG. 3C, the bio-impedance sensor 32 may comprise a plurality of vertical metallic rods that form a cylinder with an open bottom surface. As shown in FIG. 3D, the bio-impedance sensor 32 may alternatively comprise a plurality of vertical metallic rods that form a rectangular shape with an open bottom surface (e.g., two parallel rows of vertical metal rods). It is contemplated that the bio-impedance sensor 32 may comprise a plurality of metallic elements forming any desired shape (e.g., a single row of vertical metal rods). As the foregoing sensors 32 are modular, each embodiment of the EIMD 12 may incorporate any desired style of sensor 32. In similar fashion, multiple styles of insect collector 36 may be used with the EIMD 12. For instance, each EIMD 12 may employ a delta-shaped insect collector 36, similar to that shown in FIG. 3E, or a bucket-shaped insect collector 36, similar to that shown in FIG. 3F.

As mentioned above, each EIMD 12 includes a mixed circuit board 40 that automates the detection of target insects and the reporting of gathered data back to the DSS 18. A general embodiment of the mixed circuit board 40 is shown as a simplified block diagram in FIG. 4. The mixed circuit board 40 includes one or more insect detection modules 42 that interface with the one or more sensors 32. When the one or more sensors 32 generate output signals in response to the presence of a target insect, these output signals are reported to an electronic controller 44 by the one or more insect detection modules 42. The electronic controller 44 of the mixed circuit board 40 may be embodied as any type of processor capable of executing software/firmware, such as a microprocessor, digital signal processor, microcontroller, application specific integrated circuit (ASIC), field programmable gate array (FPGA), or the like. The electronic controller 44 processes information received from the one or more insect detection modules 42 (among other sources) and sends information to other EIMDs 12, the network gateway 20, and/or the base station 28 using one or more communication modules 46. One or more localization modules 48 allow each EIMD 12 to discover its own geographic location, so that its detections of target insects can be spatially localized. Furthermore, the mixed circuit board 40 may be extended and customized using one or more extension modules 50. For example, in some embodiments, each EIMD 12 may also measure relevant environmental variables, such as temperature and relative humidity. In other embodiments, the mixed circuit board 40 may also include a non-volatile memory to temporarily store information. The power controller 52 of mixed circuit board 40 supplies power (directly or indirectly) to the one or more insect detection modules 42, the electronic controller 44, the one or more communication modules 46, the one or more localization modules 48, and the one or more extension modules 50.

Figure 5:
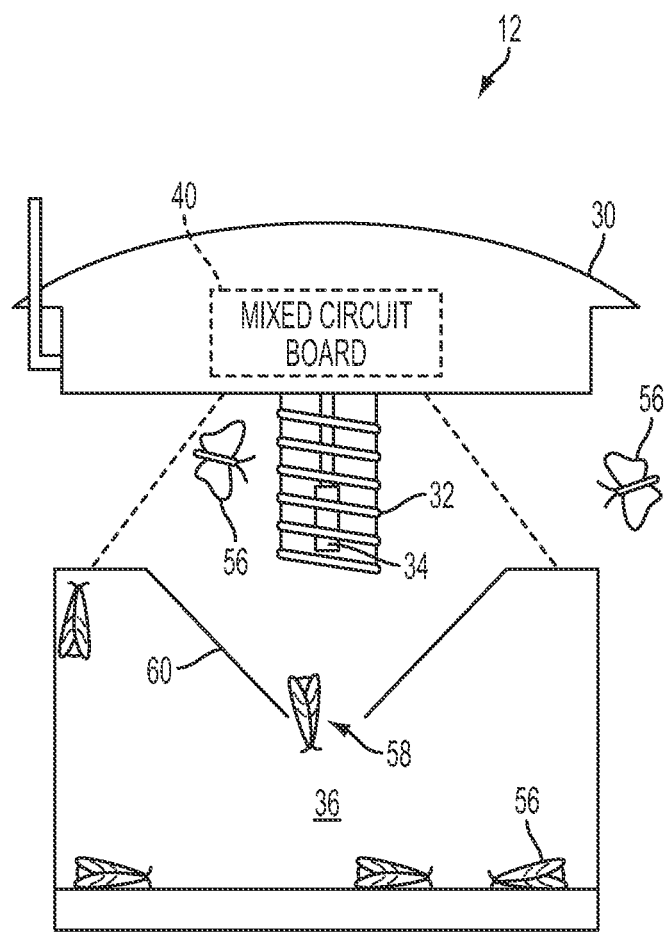
FIG. 5 is a cross-sectional schematic of another illustrative embodiment of an EIMD that may be used in the IPM system of FIG. 1.

One illustrative embodiment of an EIMD 12 that employs a bio-impedance sensor 32 and a delta-shaped insect collector 36 is shown in cross-section in FIG. 5. Similar to the high-voltage electric discharge grid 32 shown in FIG. 3B, the bio-impedance sensor 32 of FIG. 5 is illustratively embodied as a pair of metallic coils spaced approximately ⅕ inch apart from one another. It will be appreciated that, in other embodiments, the inter-coil spacing may be adjusted according to the target insect species. The EIMD 12 includes one or more lures 34 located amongst the coils to attract at least one species of target insect 56. The mixed circuit board 40 (located in the electronics housing 30) causes a voltage difference to be applied between the pair of metallic coils of the bio-impedance sensor 32, but no current normally flows, since the two coils form an open circuit. As an insect 56 approaches and/or touches the bio-impedance sensor 32, the circuit is closed, and a current flow occurs which electrocutes the target insect 56. In some embodiments, the voltage level applied to the bio-impedance sensor 32 may be optimized to temporarily stun the target insect 56, rather than completely electrocuting the target insect 56, to avoid its carcass adhering to a surface of to the bio-impedance sensor 32. Because the bio-impedance sensor 32 of FIG. 5 does not employ a supporting frame for the coils, this design avoids the accumulation of chemicals used in the field 16 that could potentially short-circuit the two coils. Furthermore, as the bio-impedance sensor 32 does not include any non-conductive landing surface, target insects 56 cannot approach the lure(s) 34 without being electrocuted (and hence detected). It will be appreciated by persons of skill in the art that foregoing considerations are equally applicable to alternative bio-impedance sensor designs, including those illustrated in FIGS. 3C and 3D.

Figure 6:
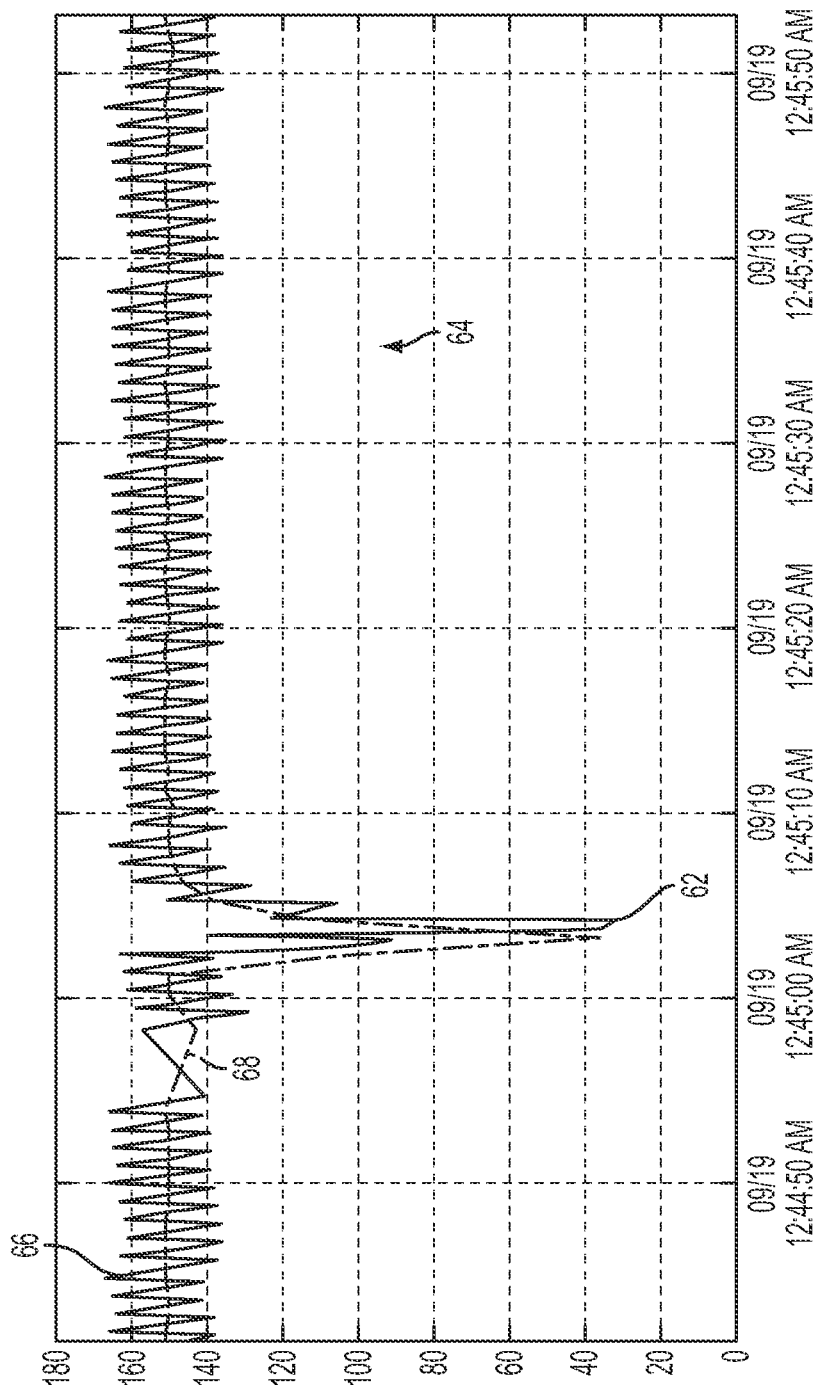
FIG. 6 illustrates an exemplary electrical pulse generated by the presence of a target insect in the EIMD of FIG. 5.

The EIMD 12 detects target insects 56 by analyzing the characteristics of the voltage and current signals at the terminals of the bio-impedance sensor 32. When a target insect 56 approaches and/or touches the coils of the bio-impedance sensor 32, an electrical pulse 62 is generated, as illustrated in FIG. 6. The graph of FIG. 6 contrasts the signal 64 generated by the bio-impedance sensor 32 during normal operation and the electrical pulse 62 caused by the detection of an insect 56. The electronic controller 44 may analyze one or more properties of each electrical pulse 62, including its slope, amplitude, rise time, fall time, width, ringing frequency, etcetera, to distinguish whether the event was caused by an insect 56 belonging to a target insect species or a non-target insect species. In embodiments using multiple lures 34, the properties of electrical pulse 62 can be used not only to distinguish target versus non-target insects 56 but also to classify the detected insect 56 as a particular target insect species. Electrical variations in the system (i.e., noise) may be eliminated by the use of a filter, such as a median filter. It will be understood that appropriate filters may implemented in discrete hardware components, in the software of the electronic controller 44, or in both. As shown in FIG. 6, applying a median filter to the unfiltered signal 66 generates a filtered signal 68 in which the small variations have been removed but the large variations resulting from the presence of an insect 56 are retained.

When an insect 56 is attracted by the one or more lures 34 and electrocuted by the bio-impedance sensor 32, the insect 56 falls into the insect collector 36 of the EIMD 12, as shown in FIG. 5. Similar to the delta-shaped insect collector 36 shown in FIG. 3E, the insect collector 36 of FIG. 5 is configured such that temporarily stunned insects 56 easily fall through an inlet 58 of the insect collector 36 but have difficulty escaping from the collector 36 due to the inwardly-sloped upper surfaces 60 of the insect collector 36. In other embodiments, a bucket-shaped insect collector 36 (similar to that shown in FIG. 3F) may be used with the EIMD 12. In either case, it is also contemplated that liquid polytetrafluoroethylene (PTFE) (commonly referred to as "Insect-A-Slip" or "Fluon"), or similar substances, may be applied to one or more surfaces of the insect collector 36 to increase the capture rate and decrease the escape rate. Application of liquid PTFE creates a slippery surface that causes target insects 56 to fall into the insect collector 36 more readily and to have more difficulty climbing out of the insect collector 36 after being captured.

Figure 7:
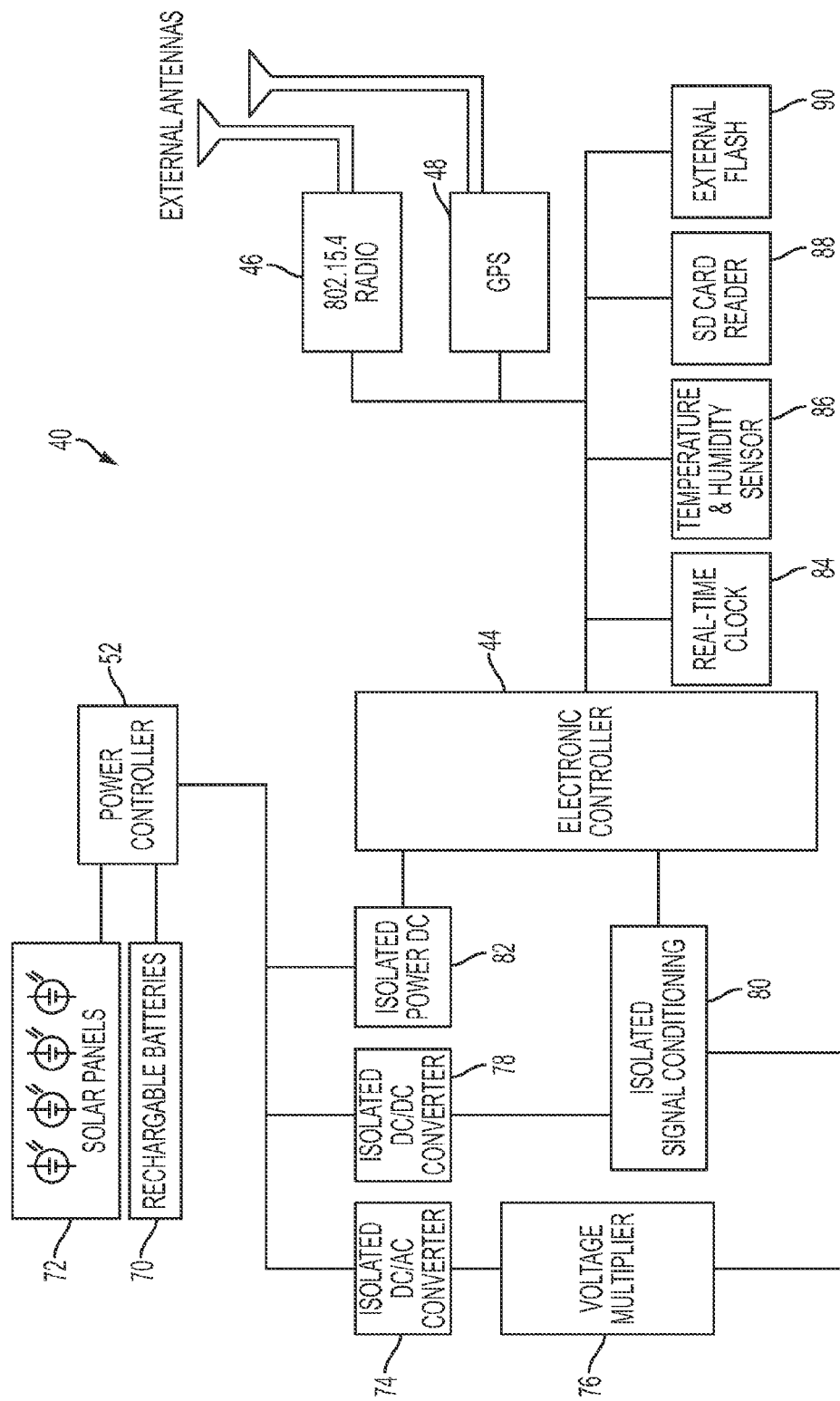
FIG. 7 is a simplified block diagram of the mixed circuit board of the EIMD of FIG. 5.

Referring now to FIG. 7, the mixed circuit board 40 of the EIMD 12 of FIG. 5 is illustrated as a simplified block diagram. In this illustrative embodiment, the mixed circuit board 40 is powered either by one or more rechargeable batteries 70, one or more solar panels 72, or both simultaneously. For example, the EIMD 12 may draw power from a number D-type rechargeable batteries or a number of lithium iron phosphate ($LiFePO_4$) rechargeable batteries. The power controller 52 provides power from the rechargeable batteries 70 and/or the solar panels 72 to the rest of the mixed circuit board 40. A DC voltage generated by the power controller 52 is converted to AC voltage by an isolated DC/AC converter 74. A voltage multiplier 76 uses this AC voltage to generate the high voltages that are applied to the bio-impedance sensor 32. An isolated DC/DC converter 78 also receives power from the power controller 52 and converts it to the appropriate levels for powering an isolated signal conditioning circuit 80. This isolated signal conditioning circuit 80 measures the output signals from the bio-impedance sensor 32 when a target insect 56 is electrocuted and delivers these measurements to an analog channel of the electronic controller 44. An isolated DC power circuit 82 supplies power from the power controller 52 to the electronic controller 44.

In some embodiments, the EIMD 12 is able to operate on battery power for at least six months, thereby eliminating the need to replace batteries during a typical growing season and further reducing labor costs. In addition to using low power microelectronic devices for data acquisition, storage, processing, and transmission, and the one or more solar panels 72 for energy harvesting, the power controller 52 may also include an adaptive duty-cycling mechanism that allows the EIMD 12 to operate during shorter periods of time when it detects that its energy reserves are low. As the power controller 52 senses that energy stored in the one or more rechargeable batteries 70 is steadily decreasing, the power controller 52 may intermittently supply power to the isolated DC/AC converter 74, the isolated DC/DC converter 78, and the isolated DC power circuit 82 for shorter periods of time. This adaptive duty-cycling mechanism allows the EIMD 12 to operate for the maximum amount of time without depleting its energy reserves, obtaining an optimal balance between battery lifetime and insect counting accuracy.

The mixed circuit board 40 of FIG. 7 also includes a wireless radio 46 that allows the EIMD 12 to communicate with other EIMDs 12, the network gateway 20, and/or the base station 28. In the illustrative embodiment, the wireless radio 46 operates according to IEEE Standard 802.15.4, Wireless Medium Access Control (MAC) and Physical Layer (PHY) Specifications for Low-Rate Wireless Personal Area Networks (LR-WPANs), the entire disclosure of which is incorporated by reference herein. It is contemplated that the wireless radio 46 may utilize other communications protocols in other embodiments. In the illustrative embodiment, the mixed circuit board 40 also includes a number of extension modules 50, such as a real time clock 84 to accurately track the current time and permit insect detections to be time stamped, one or more temperature and humidity sensors 86 to monitor relevant environmental parameters, an SD card reader 88 for local information storage, and an external flash memory 90 for local information storage. It will be appreciated that the mixed circuit board 40 may include additional or fewer extension modules 50 in other embodiments.

A GPS module 48 is also included on the mixed circuit board 40 to allow the EIMD 12 to automatically find its own location. As noted above, multiple EIMDs 12 may be deployed in a field 16 to form an EIMD network 14 for insect population monitoring. During deployment, each EIMD 12 is initialized with its own coordinates and a global time reference. This may be done in several ways. In the illustrative embodiment, each EIMD 12 includes the GPS module 48, which provides highly accurate localization but increases the overall power budget of the EIMD 12, as well as its cost. In other embodiments, a handheld GPS device may be used that transmits the coordinates and global time reference to each EIMD 12 at the time of deployment. This approach is attractive both in terms of cost and power consumption but requires a user to carry the handheld GPS device during deployment. In still other embodiments, the EIMDs 12 may determine their coordinates and the global time reference using localization algorithms, such as those described in T. H. He, Range-Free Localization Schemes for Large Scale Sensor Networks, Proc. 9th Ann. Int'l Conf. on Mobile Computing & Networking 81-85 (2003); K. R. Langendoen, Distributed Localization in Wireless Sensor Networks: A Quantitative Comparison, 43 Computer Networks, Wireless Sensor Networks 499-518 (2003); C. R.

Savarese, Location in Distributed Ad-Hoc Wireless Sensor Networks, 4 Proc. IEEE Int'l Conf. on Acoustics, Speech, & Signal Processing 2037-2040 (2001); and A. H. C. Savvides, Dynamic Fine-Grained Localization in Ad-Hoc Wireless Sensor Networks, Proc. 7th Ann. ACM/IEEE Int'l Conf. on Mobile Computing & Networking (2001), the entire disclosures of which are each incorporated by reference herein. The accuracy of such localization algorithms may be degraded in environments where there are obstacles to direct communication among the EIMDs 12 (such as the canopies of trees in the field 16).

Figure 8:
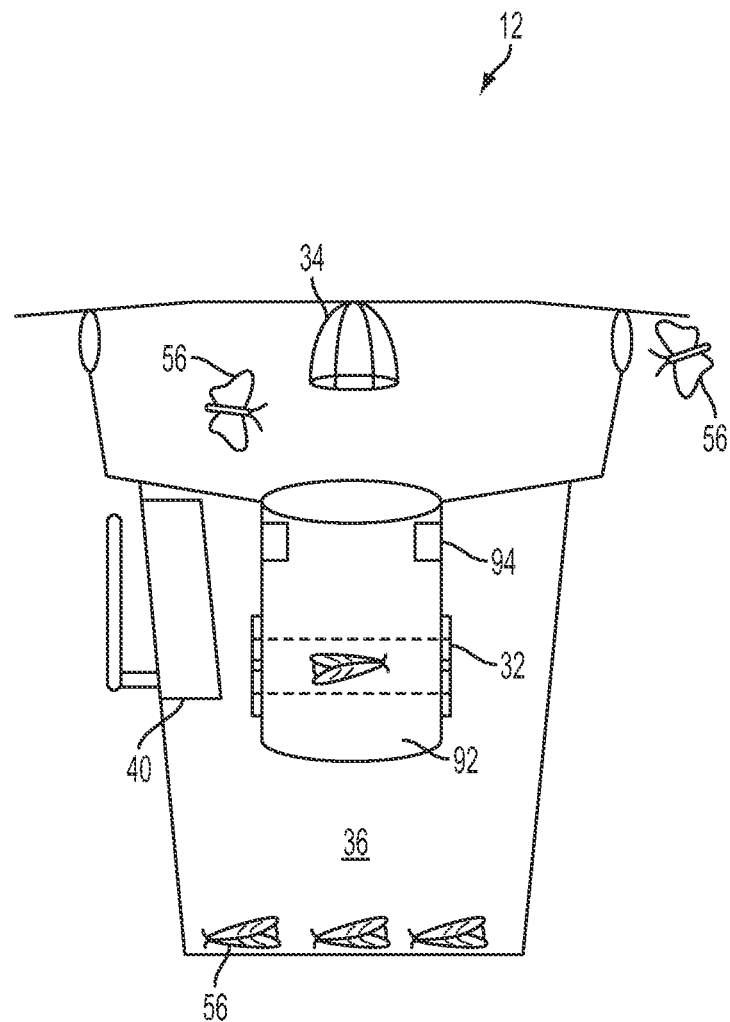
FIG. 8 is a cross-sectional schematic of yet another illustrative embodiment of an EIMD that may be used in the IPM system of FIG. 1.
Figure 9:
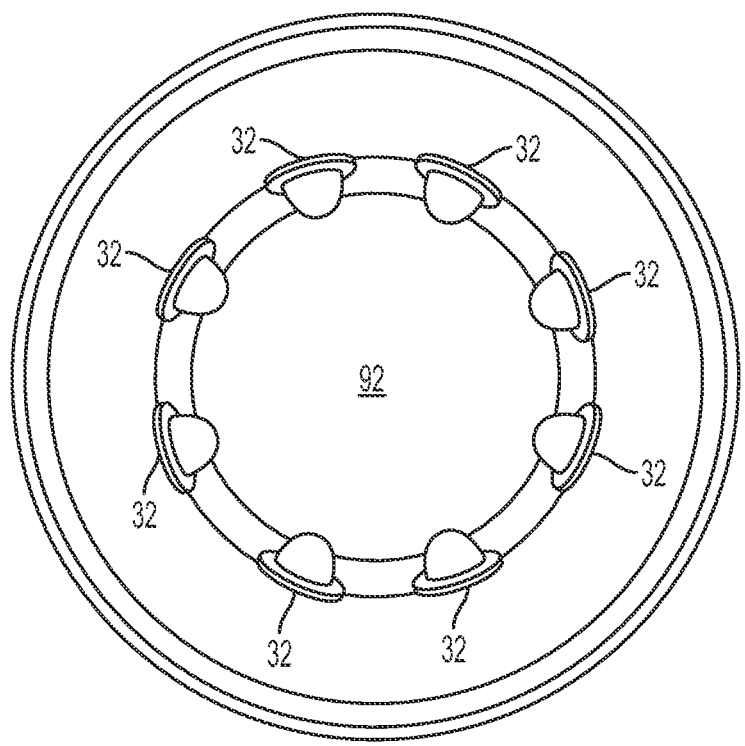
FIG. 9 illustrates the optical sensors of the EIMD of FIG. 8.
Figure 10:
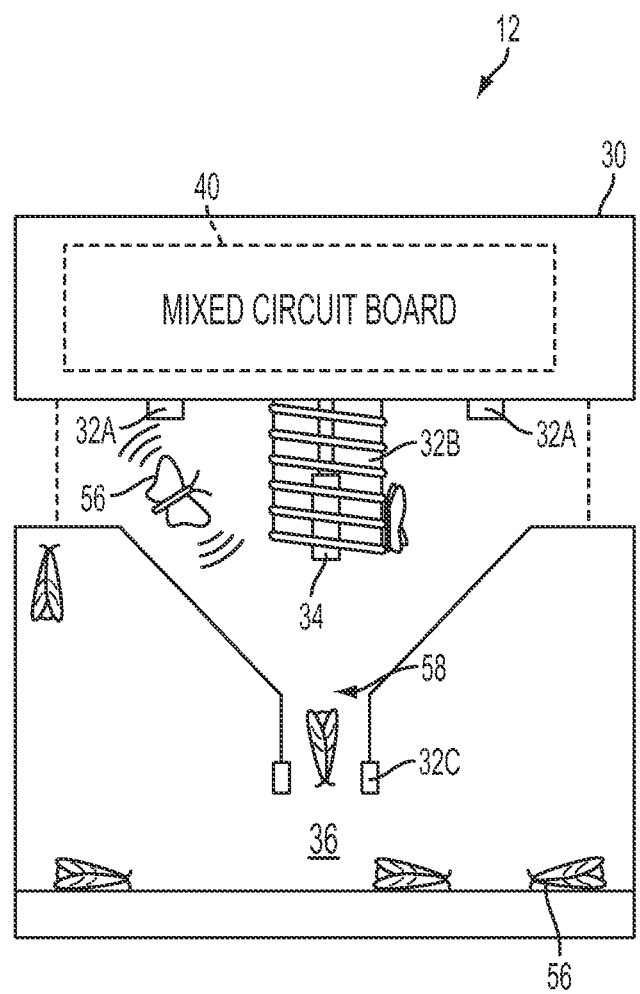
FIG. 10 is a cross-sectional schematic of still another illustrative embodiment of an EIMD that may be used in the IPM system of FIG. 1.

Another illustrative embodiment of an EIMD 12, which employs optical sensors 32 and a bucket-shaped insect collector 36, is shown in cross-section in FIG. 8. In some embodiments, the optical sensors 32 may include a number of visible-light or infrared (IR) light emitting diodes (LEDs) and corresponding detectors. For instance, an illustrative embodiment in which eight IR LEDs/detectors 32 are distributed around the circumference of a funnel 92 of the EIMD 12 is shown from a bottom view in FIG. 9. For increased accuracy, other embodiments may employ multiple concentric rings of IR LEDs/detectors 32 distributed around the circumference of the funnel 92. As target insects 56 are attracted by one or more lures 34 placed in the EIMD 12, a kill strip 94 impregnated with pesticide intoxicates the insects 56 and eventually causes them to fall through the funnel 92. The optical sensors 32 mounted in the funnel 92 (for example, near a bottom portion of the funnel 92, as shown in FIG. 8) are used to count the falling insects 56. Similar to the previously discussed embodiment, the electronic controller 44 on the mixed circuit board 40 analyzes output signals from the optical sensors 32 to determine the presence of a target insect 56 in the EIMD 12. In some embodiments, the properties of the one or more output signals received from the optical sensors 32 may be used not only to detect the presence of insects 56 but also to distinguish different species. It is contemplated that the EIMD 12 of FIG. 8 may use many of the same components as the EIMD 12 of FIG. 5 (for instance, components of the mixed circuit board 40 shown in FIG. 7). Furthermore, due to the modular nature of the components of the EIMD 12, the optical sensors 32 just described may be used with an insect collector 36 having inwardly-sloped upper surfaces 60 (similar to those shown in FIG. 5). In such embodiments, a kill strip 94 may not be needed to keep the target insects 56 from escaping the insect collector 36.

Still other illustrative embodiments of the EIMD 12 may use a plurality of multimodal sensors 32 to detect the presence and species of target insects 56. In some embodiments, such as that shown in FIG. 10, the multimodal sensors 32 may include one or more ultrasound sensors 32A, one or more bio-impedance sensors 32B, and one or more optical sensors 32C (among others types of sensors 32). The information obtained from the plurality of multimodal sensors 32 may be combined by the electronic controller 44 of the mixed circuit board 40 using sensor fusion algorithms in order to accurately identify the insect species captured. Some illustrative algorithms are described in T. Ganchev et al., Acoustic Monitoring of Singing Insects, IEEE Int'l Conf. on Acoustics, Speech & Signal Processing 721-724 (2007); M. Mayo et al., Automatic Species Identification of Live Moths, Knowledge-Based Sys. 195-202 (2007); C. F. Graetzel et al., A 6000 Hz Computer Vision System for Real-Time Wing Beat Analysis of Drosophila, R., Robotics & Biomechatronics 278-283 (2006); A. T. Watson et al., Automated Identification of Live Moths (Macrolepidoptera) Using Digital Automated Identification SYstem (DAISY), Systematics & Biodiversity 287-300 (2003); A. Moore et al., Automated Identification of Optically Sensed Aphid (Homoptera: Aphidae) Wingbeat Waveforms, Annals Entomological Soc. Amer. 1-8 (2002); E. D. Chesmore et al., Acoustic Methods for the Automated Detection and Identification of Insects, Int'l Sym. on Sensors Horticulture 223-231 (2001); and A. Moore et al., Automated Identification of Flying Insects by Analysis of Wingbeat Frequencies, J. Econ. Entomology 1703-1706 (1986), the entire disclosures of which are each incorporated by reference herein. Unlike existing devices which rely on expensive and high performance computing devices, however, the presently disclosed EIMD 12 uses low-cost, low-power sensors with detection and classification algorithms that can be run on an embedded platform for real-time processing. It is contemplated that the EIMD 12 of FIG. 10 may use many of the same components as the EIMD 12 of FIG. 5 (for instance, components of the mixed circuit board 40 shown in FIG. 7). Furthermore, due to the modular nature of the components of the EIMD 12, the multimodal sensors 32 used for a particular EIMD 12 may be easily optimized based on the species of target insect 56.

Figure 11:
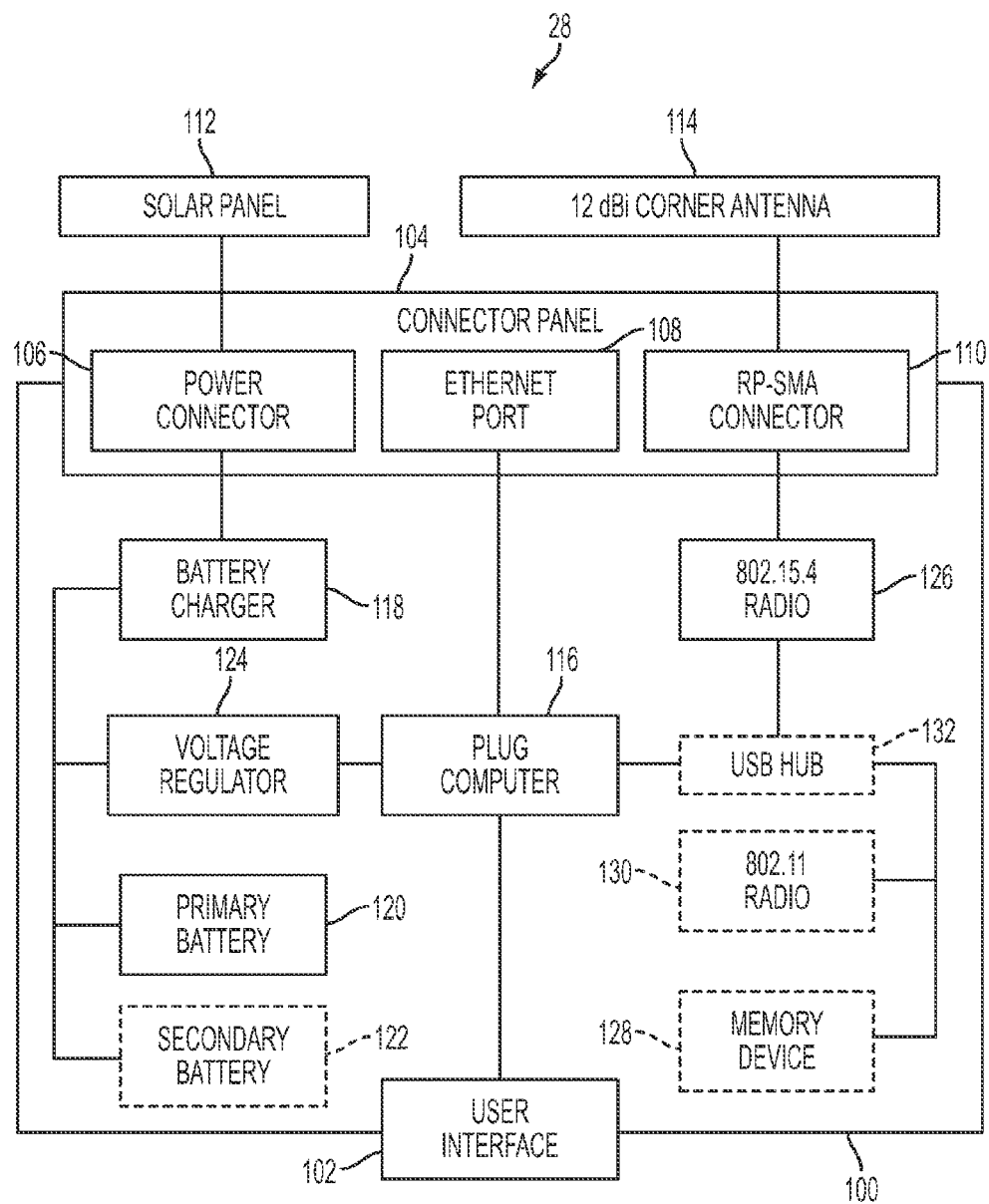
FIG. 11 is a simplified block diagram of one illustrative embodiment of an embedded base station that may be used in the IPM system of FIG. 1.

Referring now to FIG. 11, in some embodiments, the IPM system 10 may optionally include an embedded base station 28 in place of the network gateway 20. As mentioned above, in situations where the DSS 18 and network gateway 20 cannot be conveniently located in or near the field 16, the base station 28 may be deployed in the field 16 and collect data from the EIMD network 14. As the base station 28 will generally be located outdoors, the components of the base station 28 are enclosed in a weather-proof housing 100 having a weather-proof user interface 102 and a weather-proof connector panel 104. The user interface 102 may comprise a number of input and output devices, including, but not limited to, weather-proof buttons and LEDs. The connector panel 104 may comprise a number of external connector ports, such as a power connector 106, an Ethernet port 108, and a reverse-polarity, subminiature version A (RP-SMA) connector 110, by way of example. In the illustrative embodiment, the power connector 106 is coupled to one or more solar panels 112 disposed on or near the base station 28. In other embodiments, the power connector 106 may be coupled to an alternative source of power (e.g., AC mains power), if such a power source is available in the field 16. The RP-SMA connector 110 is coupled to a communications antenna 114, which is illustratively embodied as a 12 dBi corner antenna.

As shown in FIG. 11, the base station 28 comprises a small form factor computer 116 (commonly known as a "plug computer") that serves as a central processing unit of the base station 28. In one illustrative embodiment, the plug computer 116 may be a SheevaPlug device, commercially available from Globalscale Technologies, Inc. of Anaheim, Calif. A battery charger 118 of the base station 28 receives power from one or more solar panels 112 via the power connector 106 and uses this power to charge one or more rechargeable batteries 120, 122. As shown in FIG. 11, the base station 28 includes at least a primary battery 120 and may optionally include one or more secondary batteries 122. In the illustrative embodiment, both the primary and secondary batteries 120, 122 comprise LiFePO$_4$ rechargeable batteries. A voltage regulator 124 draws power from the one or more rechargeable batteries 120, 122 and supplies DC power to the plug computer 116. Using the foregoing components, the base station 28 is able to operate in the field 16 for lengthy periods of time without the need to connect to an external source of power.

The base station 28 further comprises at least one wireless radio 126 for communicating with the EIMD network 14. In the illustrative embodiment of FIG. 11, the wireless radio 126 is configured according to IEEE Standard 802.15.4 and is coupled to the communications antenna 114 via the RP-SMA connector 110. It will be appreciated that the wireless radio 126 may utilize other communications protocols in other embodiments. Using the wireless radio 126, the plug computer 116 may communicate with any EIMD 12 within the communication range of the antenna 114. As such, the base station 28 may collect data from the EIMD network 14 for storage or transmission to the DSS 18. In some embodiments, the base station may contain additional components, such as a memory device 128 and/or a second wireless radio 130. In such embodiments, a universal serial bus (USB) hub 132 may provide additional USB connections between the plug computer 116 and these additional components. The memory device 128 may be used to provide additional memory space for the plug computer 116 and may be embodied as any type of machine-readable media (e.g., flash memory). The second wireless radio 130 may be used by the plug computer 116 to communicate over the network 26. For instance, using the second wireless radio 130, the base station 28 may be configured to communicate data collected from the EIMD network 14 to the DSS 18 and/or to the computing devices 22, 24. Although the second wireless radio 130 in FIG. 11 illustratively uses the IEEE 802.11 communication standard, the second wireless radio 130 could alternatively communicate with any portion of network 26 using any number of data communication standards employed in mobile telephony. Additionally or alternatively, the base station 28 may store data for local download either to a computing device 22, 24 connected to the ethernet port 108 of the base station 28 or to a computing device 22, 24 directly within the communications range of one of the wireless radios 126, 130 of the base station 28.

Figure 12:
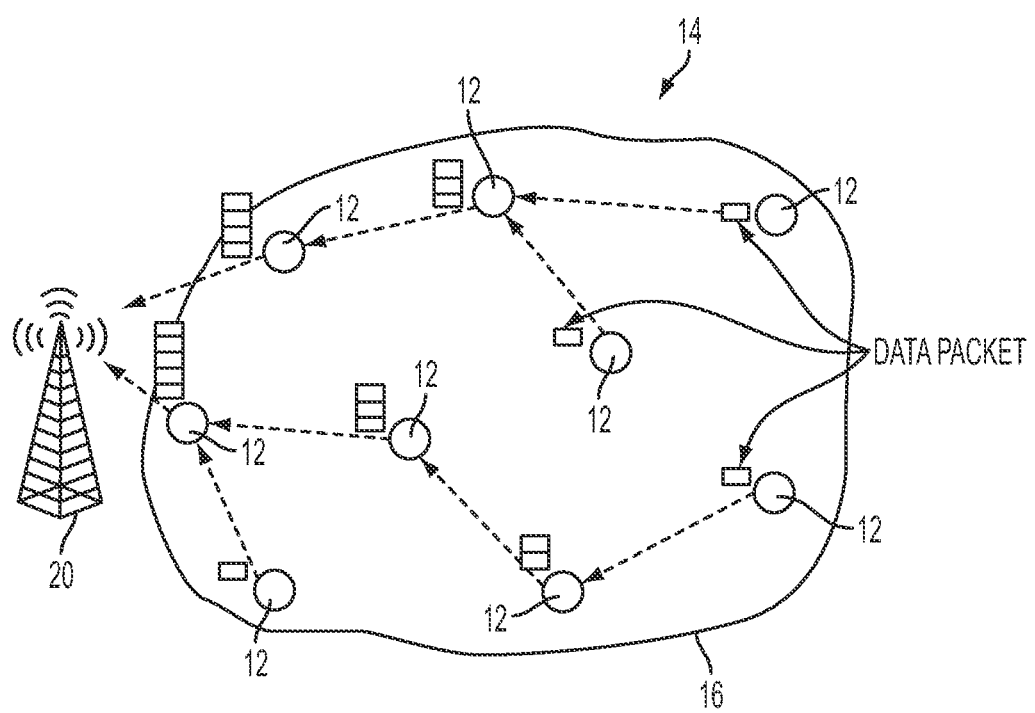
FIG. 12 illustrates one embodiment of an EIMD network that transmits data to a network gateway using multiple-hop routes.

Referring now to FIG. 12, each EIMD 12 is provided with only a limited communication range, as the amount of energy required for wireless communication increases significantly with distance. Rather than each EIMD 12 communicating directly with the network gateway 20, the information acquired by each EIMD 12 is transmitted indirectly via multiple-hop routes, as shown by the dotted lines in FIG. 12. In other words, each EIMD 12 sends the information it acquires to a neighboring EIMD 12 that is closer to the network gateway 20, which in turn forwards that information to another neighboring EIMD 12, etcetera, until the information reaches the network gateway 20. In FIG. 12, the squares near the EIMDs 12 represent the data packets containing sensor measurements acquired by individual EIMDs 12 that need to be transmitted to the network gateway 20. As illustrated in FIG. 12, without any local data aggregation and compression, the total amount of data transmitted in the network becomes significantly larger than the amount of data transmitted by the direct communication approach. Specifically, the EIMDs 12 nearer the network gateway 20 will have much greater communication loads than those far from the sink, since the size of the data packets grows as they are relayed through the EIMD network 14. This unbalanced power consumption in the network only becomes more problematic as more EIMDs 12 are added to the EIMD network 14.

The presently disclosed EIMD network 14 employs in-network data aggregation and compression algorithms for encoding temporally and spatially correlated data acquired by individual EIMDs 12, thereby significantly reducing the amount of data transmissions in the network, and consequently increasing the maximum number of possible EIMDs 12 and the maximum coverage area of the EIMD network 14. For a resource constrained embedded device, such as an EIMD 12, processing data locally is much more power efficient than transmitting data wirelessly. The distributed data aggregation protocol utilized by the EIMD network 14 takes advantage of two unique characteristics of the network: (1) communication between nearby EIMDs 12 (i.e., one-hop neighbors) is inexpensive relative to communication between distant EIMDs 12 and between most EIMDs 12 and the network gateway 20 (i.e., multi-hop neighbors) and (2) data packets routed from any two EIMDs 12 to the network gateway 20 tend to travel through at least one common routing EIMD 12 before reaching the destination.

Figure 13A:
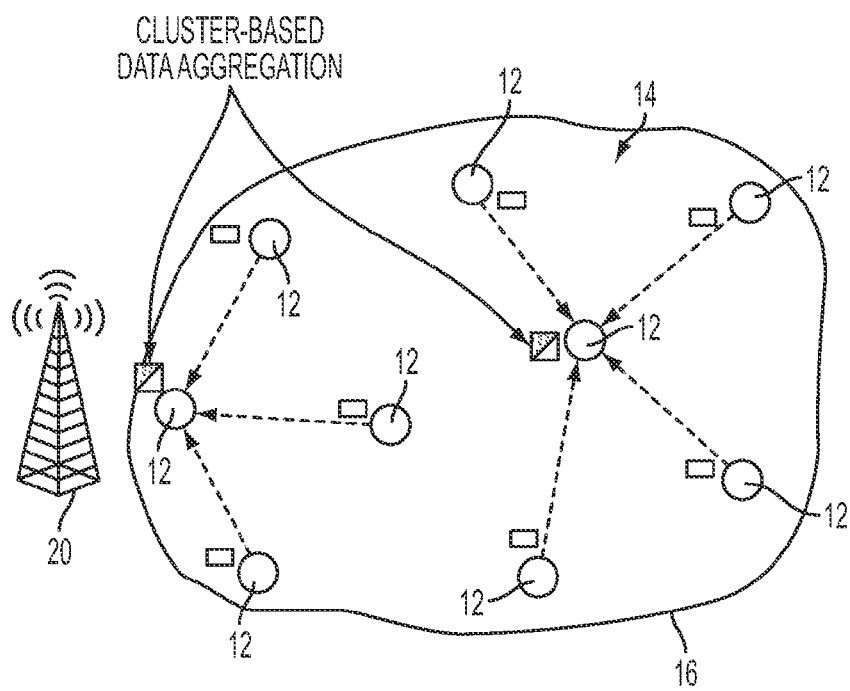
FIG. 13A illustrates the use of cluster-based data aggregation in the EIMD network of FIG. 12.

A first aspect of the distributed data aggregation protocol utilized by the EIMD network 14 is the formation of clusters of EIMDs 12 that locally aggregate data before transmitting the data to the network gateway 20. This cluster-based data aggregation approach is illustrated in FIG. 13A. As the EIMDs 12 acquire information about the insect population (and/or the environment), rather than transmitting each measurement individually to the network gateway 20 (which may be multiple hops away from the transmitting EIMD 12), each EIMD 12 transmits its own measurement to a nearby EIMD 12 (i.e., a cluster head) that aggregates the measurements it receives into a more compact form before transmitting the data to the network gateway 20. Illustrative cluster-based data aggregation protocols are described in H. Medeiros et al., Cluster-Based Object Tracking by Wireless Camera Networks, Multi-Camera Networks: Concepts & Applications (2009); H. Medeiros et al., Distributed Object Tracking Using a Cluster-Based Kalman Filter in Wireless Camera Network, IEEE J. Selected Topics Signal Processing (2008); H. Medeiros et al., A Light-Weight Event-Driven Protocols for Sensor Clustering in Wireless Camera Networks, IEEE/ACM Int'l Conf. on Distributed Smart Cameras 203-10 (2007); D. Xia et al., Near-Optimal Node Clustering in Wireless Sensor Networks for Environmental Monitoring, IEEE Advanced Networking & Applications (2007); I. Gupta et al., Cluster-Head Election Using Fuzzy Logic for Wireless Sensor Networks, Comm'n Networks & Servs. Res. Conf. 255-60 (2005); V. Mhatre et al., A Minimum Cost Heterogeneous Sensor Network with a Lifetime Constraint. IEEE Transactions on Mobile Computing 4-15 (2005); O. Fahmy et al., HEED: A Hybrid, Energy-Efficient, Distributed Clustering Approach for Ad Hoc Sensor Networks, IEEE Transactions on Mobile Computing 366-79 (2004); V. Mhatre et al., Design of Surveillance Sensor Grids with a Lifetime Constraint, Eur. Workshop on Wireless Sensor Networks (2004); P. V. Rickenbach et al., Gathering Correlated Data in Sensor Networks, Workshop on Discrete Algothrithms & Methods for MOBILE Computing & Comm'ns 60-66 (2004); S. Bandyopadhyay et al., An Energy Efficient Hierarchical Clustering, IEEE INFOCOM 1713-23 (2003); K. Kalpaski et al., Efficient Algorithms for Maximum Lifetime Data Gathering and Aggregation in Wireless Sensor Networks, Computer Networks 697-716 (2003); W. B. Heinzelman et al., An Application-Specific Protocol Architecture for Wireless Microsensor Networks, 1 660-670 (2002); and W. B. Heinzelman et al., Energy-Efficient Communication Protocol for Wireless Microsensor Networks, Ann. Ha. Int'l Conf. on Sys. Sci. (2000), the entire disclosures of which are each incorporated by reference herein.

Measurements obtained by the EIMD network 14 are characterized by data locality. In other words, the benefits of sharing information among nearby EIMDs 12 are much higher than those of sharing information with distant EIMDs 12. Based on this characteristic, sharing information only between one-hop neighbors for the purpose of data compression results in a highly effective data compression scheme. Since the "cluster head" EIMDs 12 are responsible for data aggregation and compression, they may drain their batteries more quickly than the other EIMDs 12 (i.e., the "cluster members"). In order to balance the overall energy consumption rate in the EIMD network 14, the role of cluster head may be dynamically assigned to different EIMDs 12 throughout the lifespan of the EIMD network 14.

Figure 13B:
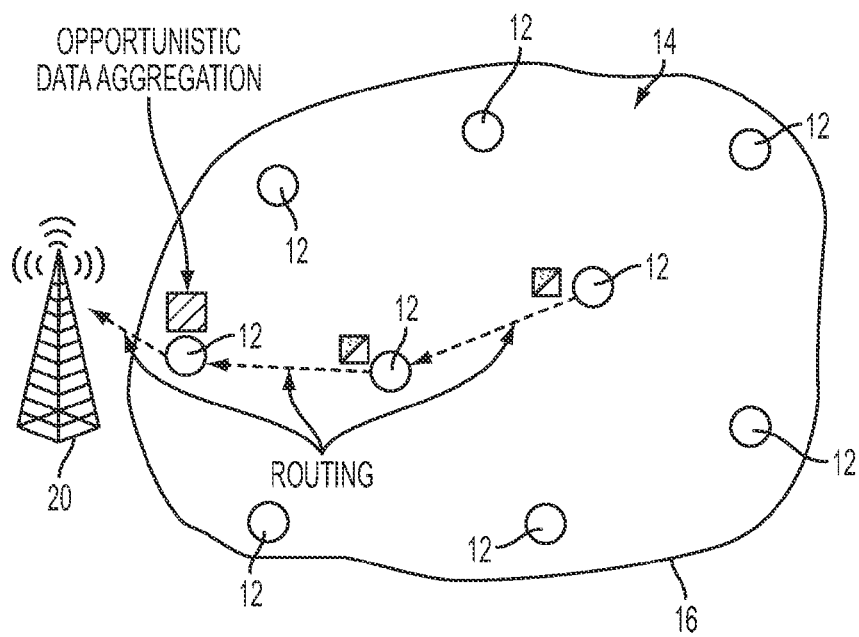
FIG. 13B illustrates the use of opportunistic data aggregation in the EIMD network of FIG. 12.

A second aspect of the distributed data aggregation protocol utilized by the EIMD network 14 is the aggregation of multiple data packets that happen to meet at a common EIMD 12 into a new, more compact data packet before transmitting the data to the network gateway 20. This opportunistic data aggregation approach is illustrated in FIG. 13B. Even though the correlation among the data received from distant EIMDs 12 tends to be smaller than that of nearby EIMDs 12, opportunistic data aggregation may still provide significant energy savings, as described in C. Intanagonwiwat et al., Impact of Network Density on Data Aggregation in Wireless Sensor Networks, Distributed Computing Sys. 457-59 (2002) and L. Krishnamachari et al., The impact of Data Aggregation in Wireless Sensor Networks, Distributed Computing Sys. Workshops 575-78 (2002), the entire disclosures of which are each incorporated by reference herein. This approach also reduces the imbalance in energy depletion in the EIMD network 14 by reducing the effective size of messages as they travel toward the network gateway 20. While opportunistic data aggregation may increase message transmission latency, low latency is not as critical in agricultural monitoring applications, such as the IPM system 10.

Once again, the distributed data aggregation protocol described above is based on two fundamental characteristics of the information collected by the EIMDs 12 in the field 16: temporal correlation and spatial correlation. Regarding temporal correlation, most of the physical parameters observed by each EIMD 12 in the EIMD network 14 are governed by natural variations of the environment, and the variability of these parameters is therefore relatively predictable. These variations can be modeled using simple (i.e., continuous and well-behaved) mathematical functions. In other words, a set of large sample measurements may be transformed into a significantly compact representation using standard data-fitting techniques. For example, a few thousand temperature measurements acquired by an EIMD 12 over several hours could be represented by a few tens of parameters using a piecewise linear interpolation mechanism. In other embodiments, the EIMDs 12 may employ entropy-based compression techniques, such as those described in F. Marcelloni et al., "An Efficient Lossless Compression Algorithm for Tiny Nodes of Monitoring Wireless Sensor Networks," 52 The Computer Journal 969-87 (2009), the entire disclosure of which is incorporated by reference herein.

Similarly, measurements acquired by all the EIMDs 12 in the EIMD network 14 at a particular time instant can be considered as a two-dimensional function in which the coordinates of the EIMDs 12 (i.e., their physical locations) are the free variables. Thus, the information acquired by the EIMDs 12 may be further compressed by employing multidimensional data fitting mechanisms, as described in S. Pattern et al., The Impact of Spatial Correlation on Routing with Compression in Wireless Sensor Networks, ACM Transactions on Sensor Networks 1-33 (2008), the entire disclosure of which is incorporated by reference herein.

Furthermore, methods used in lossy image and video compression such as the discrete cosine transform (DCT) and the 3D-DCT may be employed by the EIMD network 14 to further compress the data acquired by the EIMDs 12 when some accuracy loss can be tolerated in exchange for extended network life span, as described in Y. Q. Shi, Image and Video Compression for Multimedia Engineering: Fundamentals, Algorithms, and Standards (2008), the entire disclosure of which is incorporated by reference herein. It will be appreciated that, although the distributed data aggregation protocol has been described with respect to embodiments in which the EIMD network 14 transmits collected data to a network gateway 20, the above description is equally applicable to embodiments in which the EIMD network 14 transmits collected data to an embedded base station 28 of the IPM system 10.

Figure 14A:
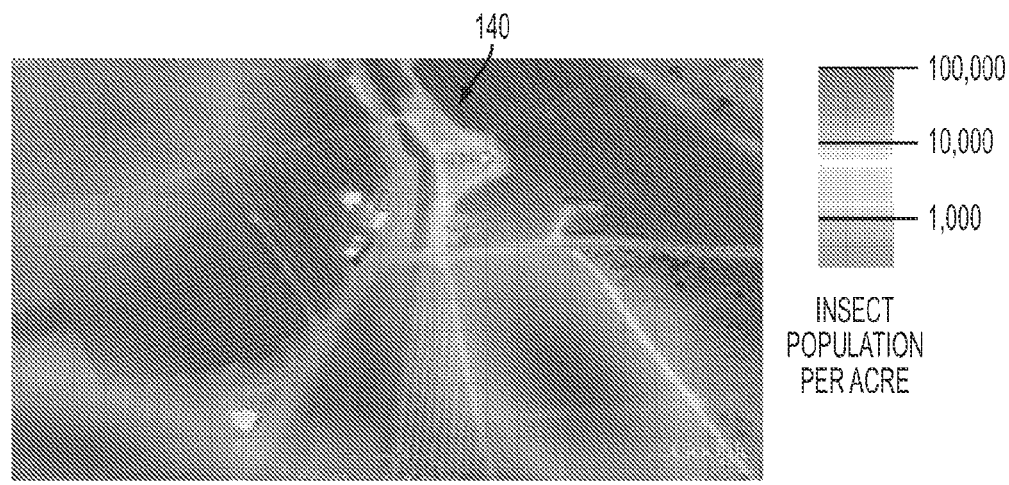
FIG. 14A illustrates one embodiment of a graphical user interface including an insect population map.
Figure 14B:
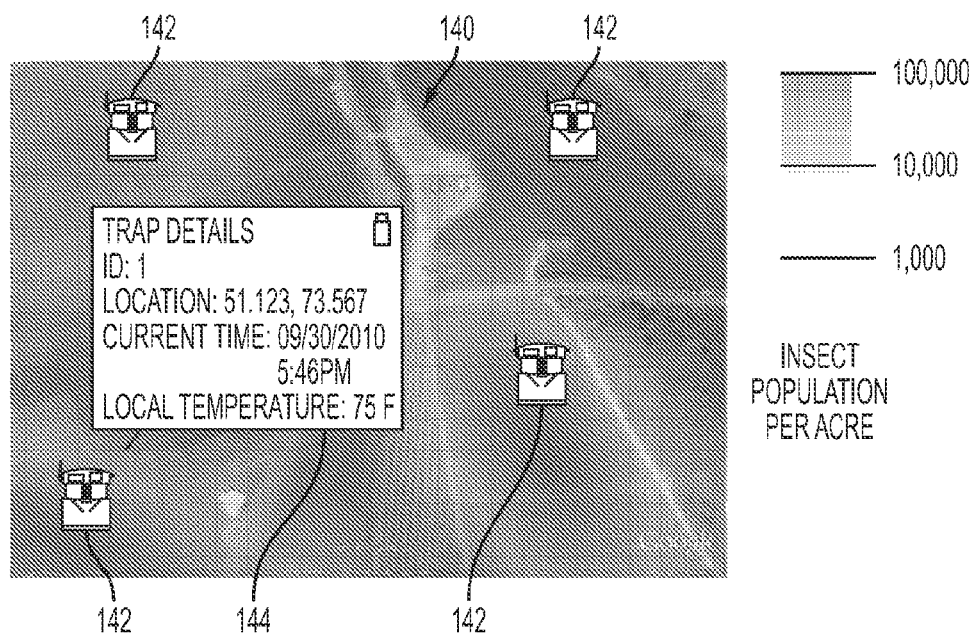
FIG. 14B illustrates another embodiment of a graphical user interface including an insect population map with the locations of EIMDs displayed as icons.

As described above, each EIMD 12 in the illustrative embodiment is able to identify the species of an insect 56 present in the trap, count the number of different target insects 56 detected, and associate the detections with a particular time and location. The EIMDs 12 transmit this data to the network gateway 20 (or the base station 28), which in turn relays this data to the DSS 18. Using the information collected by the EIMD network 14, the DSS 18 may construct a map 140 of an insect population in the monitored area at any given time. The insect population map 140 may be constructed periodically or on-demand in response to a query from a user device. Such maps may be displayed as a part of a GUI on one or more browser-enabled computing devices, such as the personal computer 22 or the mobile phone 24. In some embodiments, the insect population map 140 may include a color-coded graph (similar to an infrared map or image) overlaid on an aerial view of the monitored area. FIG. 14A illustrates one embodiment of a GUI including this type of insect population map 140. In other embodiments, the insect population map 140 may additionally display the locations of the EIMDs 12 as icons 142, as illustrated in FIG. 14B. In the embodiment of FIG. 14B, a user can see a pop-up box 144 with detailed information by clicking or mousing-over one of the icons 142 representing a particular EIMD 12. This detailed information may include, but is not limited to, the trap ID, the location (latitude and longitude), the current time in the local clock, the remaining battery charge, and the temperature.

Figure 15:
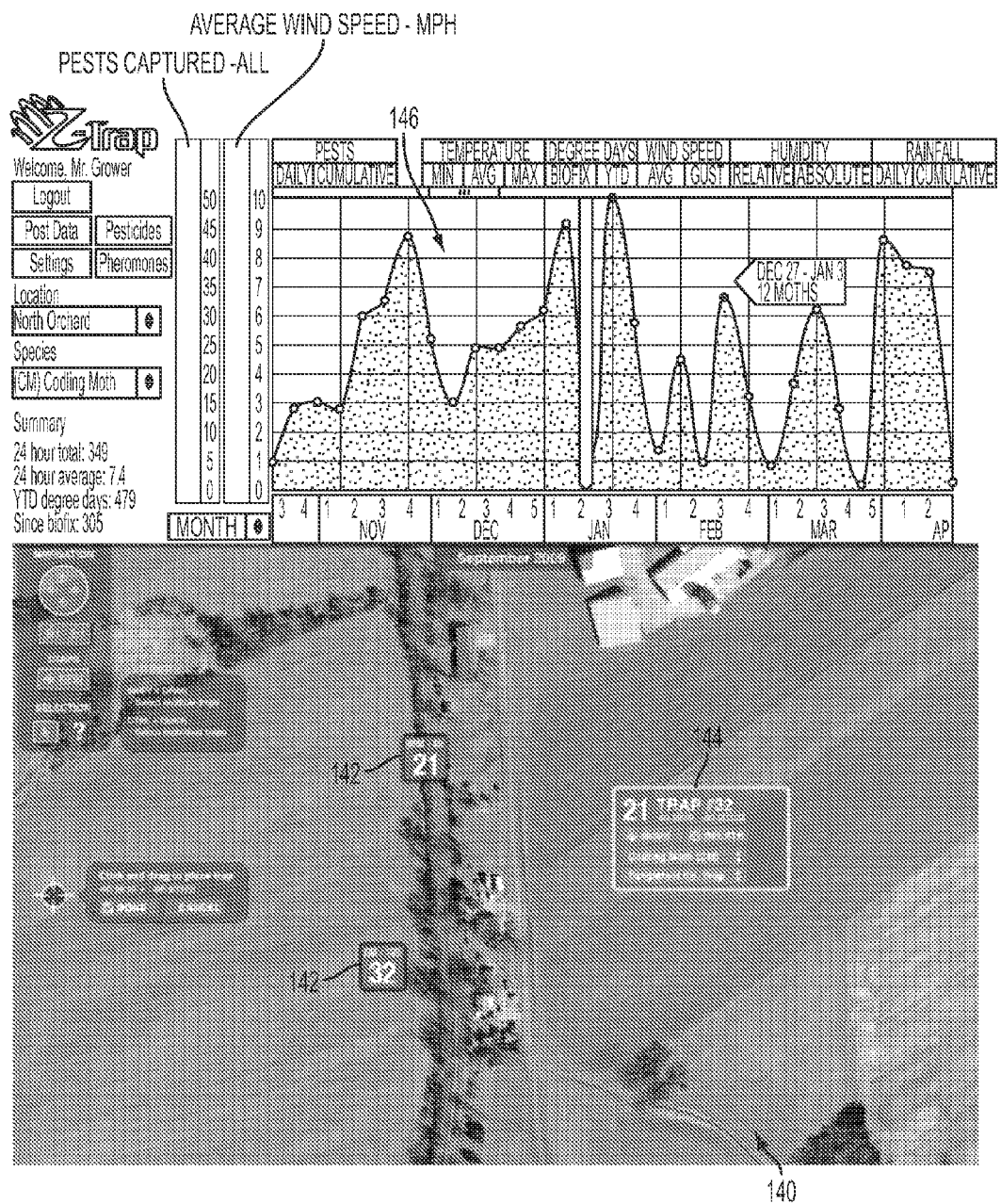
FIG. 15 illustrates yet another embodiment of a graphical user interface including an insect population map and a graph showing variations in the insect population over time.

In still other embodiments, the GUI may display icons 142 with the individual number of detections at each EIMD 12. FIG. 15 illustrates one embodiment of a GUI including this type of insect population map 140. In addition, the GUI may display a graph 146 with the variation over time of the detected target insects 56, as shown in FIG. 12. The graph 146 may indicate the variation at each individual EIMD 12, as well as the average variation over the entire EIMD network 14 or some user-selected subset of the EIMD network 14. The graph 146 may display information corresponding to one or more EIMDS 12 selected by the user overlaid on information corresponding to the entire EIMD network 14. The GUI may allow a user to adjust the zoom level of map 140 and the time scale of graph 146, among other configurable features. It will be appreciated that any of the GUIs discussed above might also be used to display other measurements obtained by the EIMDs 12, such as local temperature or relative humidity (in addition to detections of target insects 56). The GUI may also be configured to allow the user to send configuration parameters to one or more EIMDs 12, including, but not limited to, daily operating hours, reporting frequency, target insect to be monitored, etcetera. It is also contemplated that a user may utilize the GUIs above to manually enter information related to any EIMD 12 that is not in wireless communication with the DSS 18.

Those of ordinary skill in the art will appreciate that the presently disclosed IPM system 10 will significantly reduce the cost of monitoring insect populations by automating the most difficult and labor-intensive operations associated with this task. Furthermore, the presently disclosed IPM system 10 also provides unprecedented real-time, high-resolution insect population information to growers. In addition to the field of population monitoring for IPM decision support, the disclosed technology has a number of other potential applications, including, but not limited to, early detection of various insect species, mapping pest distribution, mapping insecticide resistance frequency, and monitoring beneficial insects and predators or natural enemies. These and other potential applications are described in F. Mathieu et al., Progression in Field Infestation Is Linked with Trapping of Coffee Berry Borer, J. Applied Entomology 535-40 (1999); Y. Gazit et al., Trapping Females of the Mediterranean Fruit Fly (Diptera: Tephritidae) in Israel: Comparison of Lures and Trap Type, J. Econ. Entomology 1355-59 (1998); B. Drukker et al., Do Anthocorid Predators Respond to Synomones from Psylla-Infested Pear Trees Under Field Conditions? *Entomologia experimentalis et applicata* 193-203 (1995); and H. Riedl et al., Monitoring Susceptibility to Azinphosmethyl in Field Populations of the Codling Moths (Lepidoptera: Tortricidae) with Pheromone Traps, J. Econ. Entomology 693-99 (1985), the entire disclosures of which are each incorporated by reference herein.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected. There are a plurality of advantages of the present disclosure arising from the various features of the apparatus, systems, and methods described herein. It will be noted that alternative embodiments of the apparatus, systems, and methods of the present disclosure may not include all of the features described yet still benefit from at least some of the advantages of such features. Those of ordinary skill in the art may readily devise their own implementations of the apparatus, systems, and methods that incorporate one or more of the features of the present invention and fall within the spirit and scope of the present disclosure as defined by the appended claims.

What is claimed is:

1. An electronic insect monitoring device (EIMD) comprising:
    a lure for attracting at least one target insect species;
    one or more bio-impedance sensors configured to generate one or more output signals in response to an insect approaching the lure, the one or more bio-impedance sensors comprising a high-voltage electric discharge grid; and
    an electronic controller configured to determine if the insect approaching the lure belongs to the at least one target insect species using the one or more output signals.

2. The EIMD of claim 1, wherein the high-voltage electric discharge grid comprises a plurality of metallic elements that define a cylinder with an open bottom surface.

3. The EIMD of claim 2, wherein the plurality of metallic elements of the high-voltage electric discharge grid comprises a plurality of concentric helical coils.

4. The EIMD of claim 2, wherein the plurality of metallic elements of the high-voltage electric discharge grid comprises a plurality of vertical rods.

5. The EIMD of claim 1, wherein the high-voltage electric discharge grid is configured to produce a voltage that only temporarily stuns an insect that approaches the lure.

6. The EIMD of claim 1, wherein the electronic controller is configured to determine if the insect approaching the lure belongs to the at least one target insect species by analyzing at least one of a slope, an amplitude, a rise time, a fall time, a width, and a ringing frequency of an electrical pulse of the one or more output signals.

7. The EIMD of claim 1, further comprising one or more additional sensors selected from the group consisting of ultrasonic sensors and optical sensors, the one or more additional sensors configured to generate one or more output signals in response to an insect approaching the lure.

8. The EIMD of claim 7, wherein the electronic controller is configured to determine if the insect approaching the lure belongs to the at least one target insect species by applying a sensor fusion algorithm to the one or more output signals generated by the one or more bio-impedance sensors and the one or more additional sensors.

9. The EIMD of claim 1, further comprising a communication module for wirelessly communicating with neighboring EIMDs.

10. The EIMD of claim 1, further comprising a global positioning system module for determining a deployment location of the EIMD.

11. The EIMD of claim 1, further comprising a battery that supplies power to the electronic controller and to the one or more sensors via a power controller, wherein the power controller is configured to implement an active duty-cycling scheme to conserve the power supplied by the battery.

12. The EIMD of claim 1, further comprising an insect collector having at least one inwardly sloped upper surface.

13. The EIMD of claim 1, further comprising a housing containing the electronic controller, wherein the housing is configured to be interchangeably fitted with one of a delta-shaped insect collector and a bucket-shaped insect collector.

14. The EIMD of claim 1, wherein the at least one target insect species comprises one or more moth species.

15. The EIMD of claim 1, wherein the at least one target insect species comprises one or more of *Cydia pomonella*, *Grapholita molesta*, *Archips argyrospila*, and *Choristoneura rosaceana*.

16. The EIMD of claim 1, wherein the at least one target insect species comprises one or more of *Plodia interpunctella*, *Ephestia kuehniella*, *Lasioderma serricorne*, and *Trogoderma variabile*.

17. The EIMD of claim 1, wherein the high-voltage electric discharge grid comprises a plurality of vertical metallic rods that define a polyhedron with an open bottom surface.

18. An electronic insect monitoring device (EIMD) comprising:
    a lure for attracting at least one target insect species;
    one or more sensors configured to generate one or more output signals in response to an individual insect approaching the lure; and
    an electronic controller configured to (i) determine if each individual insect approaching the lure belongs to the at least one target insect species using the one or more output signals and (ii) count a total number of individual insects approaching the lure that belong to the at least one target insect species.

19. The EIMD of claim 18, wherein the at least one target insect species comprises one or more moth species.

20. The EIMD of claim 18, wherein the at least one target insect species comprises one or more of *Cydia pomonella, Grapholita molesta, Archips argyrospila*, and *Choristoneura rosaceana*.

21. The EIMD of claim 18, wherein the at least one target insect species comprises one or more of *Plodia interpunctella, Ephestia kuehniella, Lasioderma serricorne*, and *Trogoderma variabile*.

* * * * *